United States Patent [19]
Rehwinkel et al.

[11] Patent Number: 5,625,067
[45] Date of Patent: Apr. 29, 1997

[54] CYCLOPENTANE ETHER DERIVATIVES, PROCESSES FOR THEIR PRODUCTION, AND THEIR PHARMACEUTICAL USE

[75] Inventors: Hartmut Rehwinkel; Ulrich Klar; Helmut Vorbruggen; Karl-Heinz Thierauch; Peter Verhallen, all of Berlin, Germany

[73] Assignee: Schering Aktiengesellschaft, Berlin, Germany

[21] Appl. No.: 64,134

[22] PCT Filed: Nov. 23, 1991

[86] PCT No.: PCT/DE91/00925

§ 371 Date: Dec. 14, 1994

§ 102(e) Date: Dec. 14, 1994

[87] PCT Pub. No.: WO92/09573

PCT Pub. Date: Jun. 11, 1992

[30] Foreign Application Priority Data

Nov. 23, 1990 [DE] Germany .................. 40 37 941.8

[51] Int. Cl.$^6$ .................................. C07D 215/00
[52] U.S. Cl. .................. 546/152; 546/257; 548/252; 548/237; 549/357; 549/397; 554/103; 554/104; 554/105; 554/106; 554/114; 554/88; 554/221; 554/222; 560/15; 560/24; 560/121
[58] Field of Search ................. 554/221, 103, 554/104, 105, 106, 114, 88, 222; 560/15, 24, 121; 548/237, 252; 549/335, 397; 546/152, 257

[56] References Cited

PUBLICATIONS

Cave et al., JCS, Perkins I, pp. 646–652 1981.

Cave et al., "Total Synthesis of Prostaglandin–$F_{2\alpha}$, and the 9,O–Benzyl Derivatives of Prostaglandins–$F_2\alpha$, –$F_1\alpha$, –$D_2$, and –$D_1$", *Journal of Chemical Society* (1981), pp. 646–652, see the whole article.

*Primary Examiner*—Deborah D. Carr
*Attorney, Agent, or Firm*—Millen, White, Zelano, & Branigan, P.C.

[57] ABSTRACT

The invention relates to cyclopentane ether derivatives of Formula I their salts with physiologically compatible bases, as well as the α-, β- or γ-cyclodextrin clathrates, and also the liposome-encapsulated compounds of Formula I, processes for their production, and their pharmaceutical usage.

12 Claims, No Drawings

CYCLOPENTANE ETHER DERIVATIVES, PROCESSES FOR THEIR PRODUCTION, AND THEIR PHARMACEUTICAL USE

This application is a 371 of PCT/DE91/00925 filed Nov. 23, 1991.

SPECIFICATION

The invention relates to cyclopentane ether derivatives, processes for their production, as well as their use as auxiliary agents for pharmacological studies and as medicinal agents.

Cyclopentane derivatives have been the subject of intensive scrutiny in recent years because prostaglandins derived from the cyclopentane system, such as, for example, $PGA_2$, $PGB_2$, $PGE_2$, 6-oxo-$PGE_1$, $PGD_2$, $PGF_{2\alpha}$, $PGJ_2$, and their analogs exhibit a great variety of biological effects, for example, on the cardiovascular, CNS, or immune system.

It has been found surprisingly that, by the introduction of an ether residue in position 9 (prostaglandin numbering) of the prostane skeleton in combination with a great variety of different structural features in the bottom chain, as well as in the 11 position, chemically and metabolically stable prostaglandin analogs are obtained capable of antagonizing the pharmacological properties of the unstable thromboxane $A_2$ ($TXA_2$) and, respectively, $PGH_2$, as well as its stable analogs, such as, for example U46619 or U44069 on the receptor.

Consequently, the compounds of this invention represent valuable auxiliary agents for the selective therapy of diseases that can be traced back to an excess of $TXA_2$ and, respectively, $PGH_2$.

The invention relates to cyclopentane ether derivatives of Formula I

(I)

wherein $R^1$ means

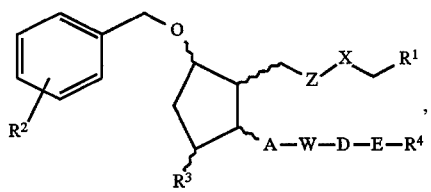

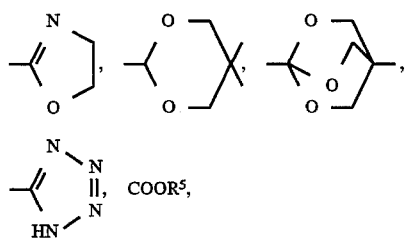

wherein $R^5$ can be hydrogen or $C_1$-$C_{10}$-alkyl optionally substituted by halogen, phenyl, $C_1$-$C_4$-alkoxy or di-($C_1$-$C_4$)-alkylamino, $C_5$-$C_6$-cycloalkyl, $C_7$-$C_{16}$-aralkyl, Y-substituted-phenacyl or-$C_6$-$C_{12}$-aryl, or a 5- or 6-membered heterocyclic residue with at least one N, O or S atom, or —$CONHR^7$ wherein $R^7$ means hydrogen, $C_1$-$C_{10}$-alkanoyl or $C_1$-$C_{10}$-alkanesulfonyl, Z is a direct bond, (Z)—CH=CH—, (E)—CH=CH—, —C≡C—, X is —$(CH_2)_p$—, —$CH_2$—O—, —$CH_2$—S—, p is 0 to 5, $R^2$ is Y or

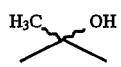

$R^3$ is hydrogen, F, $R^6$ or $OR^6$,

A is a direct bond, (Z)—CH=CH—, (E)—CH=CH—, —C≡C—,

W is a direct bond, a —$[(CH_2)_n$—V$]_q$ group, or a —$(CH_2)_n$—V—$(CH_2)_q$—V group, a free or functionally modified hydroxymethylene group, a free or functionally modified $$\underset{H_3C}{\diagdown}\underset{}{\diagup}\underset{}{\diagdown}OH$$

group wherein the hydroxy group can in each case be in the α- or β-position, q is 1 or 2, n is 0 to 2, D is a direct bond, a straight-chain saturated alkylene group of 1–5 carbon atoms, a branched saturated alkylene group, or a straight-chain or branched unsaturated alkylene group of 2–5 carbon atoms which can optionally be substituted by fluorine atoms,

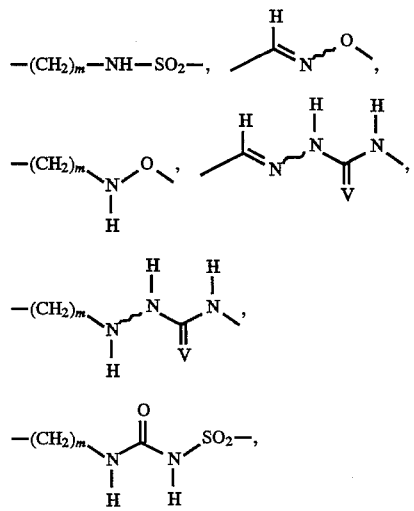

m is 0 to 2,

V is an O or S atom,

E is a direct bond, —C≡C— or —CH=$CR^8$ wherein $R^8$ means hydrogen, $C_1$-$C_5$-alkyl, halogen, or trifluoromethyl, AW, DE, independently of each other, mean a direct bond,
$R^4$ is Y-substituted $C_1$–$C_{10}$-alkyl, $C_3$–$C_{10}$-cycloalkyl,

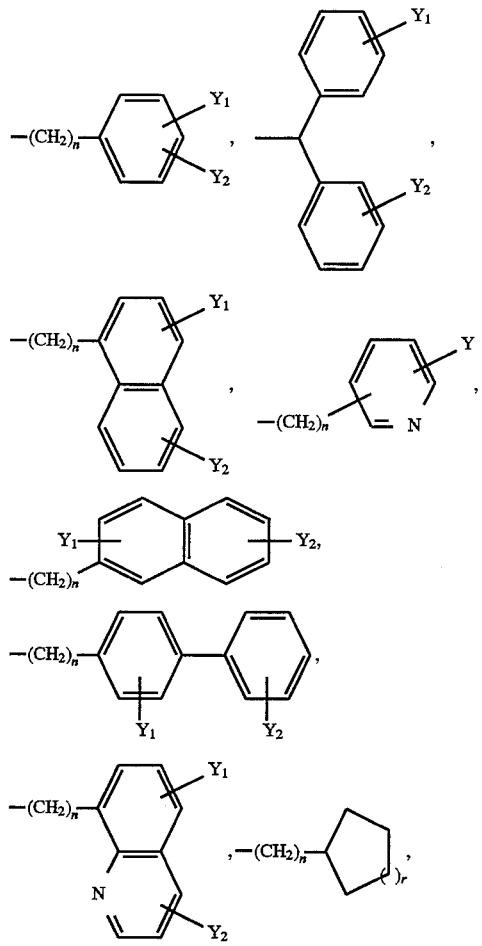

r is 1 or 2, $Y_1$ and $Y_2$, being identical or different, mean Y,

Y means hydrogen, halogen, CN, $N_3$, $CF_3$, $OR^6$, $NO_2$, —$CH_2$—$OR^6$ $COOR^6$ or $C_1$–$C_{10}$-alkyl, $R^6$ is hydrogen, $C_1$–$C_{10}$-alkyl, halogen-substituted $C_6$–$C_{12}$-aryl or $C_7$–$C_{16}$-aralkyl and, if $R^5$ means hydrogen, the salts thereof with physiologically compatible bases, as well as the α-, β- or γ-cyclodextrin clathrates, and also the liposome-encapsulated compounds of Formula I.

The definition of 5- or 6-membered heterocyclic residue concerns heterocycles containing at least one hetero atom, preferably nitrogen, oxygen, or sulfur, and being mono- or bicyclic. Examples that can be mentioned are 2-furyl, 3-furyl, 2-thienyl, 3-thienyl, 2-pyridyl, 3-pyridyl, 4-pyridyl, quinolyl, isoquinolyl.

Suitable alkyl groups $R^4$, $R^5$, $R^6$ and Y are straight- or branched-chain alkyl groups of 1–10 C atoms, such as, for example, methyl, ethyl, propyl, isopropyl, butyl, isobutyl, tert-butyl, pentyl, isopentyl, neopentyl, heptyl, hexyl, decyl.

The alkyl groups $R^4$, $R^5$, $R^6$ and Y can be substituted by halogen atoms, hydroxy groups, $C_1$–$C_4$-alkoxy groups, $C_6$–$C_{12}$-aryl groups which can be substituted by halogen, di-($C_1$–$C_4$)-alkylamines and tri-($C_1$–$C_4$)-alkylammonium. Alkyl groups which are monosubstituted are preferred.

Examples of substituents are fluorine, chlorine or bromine atoms, phenyl, dimethylamino, diethylamino, methoxy, ethoxy.

Preferred alkyl groups $R^4$, $R^5$, $R^6$ and Y are those of 1–4 carbon atoms, such as, for example, methyl, ethyl, propyl, isobutyl, butyl.

Examples for aryl groups $R^5$ and $R^6$ are: phenyl, diphenyl, 1-naphthyl and 2-naphthyl which can all be substituted by 1–3 halogen atoms, a phenyl group, 1–3 alkyl groups of respectively 1–4 carbon atoms, a chloromethyl, fluoromethyl, carboxy, $C_1$–$C_4$-alkoxy or hydroxy group. Preferred is the substitution in the 3- and 4-positions on the phenyl ring, for example by fluorine, chlorine, $C_1$–$C_4$-alkoxy or trifluoromethyl, or in the 4-position by hydroxy.

The cycloalkyl groups $R^4$ and $R^5$ can contain, in the ring, 3–10, preferably 3–6 carbon atoms. The rings can be substituted by alkyl groups of 1–4 carbon atoms. Examples that can be cited are cyclopropyl, cyclobutyl, cyclopentyl, cyclohexyl, methylcyclopentyl, methylcyclohexyl.

The $C_1$–$C_{10}$-alkyl groups mentioned under the definitions are to be straight-chain or branched alkyl groups as cited above for the aforementioned alkyl groups.

The hydroxy groups in $R^2$, $R^3$ and Y can be functionally modified, for example by etherification or esterification wherein the free or modified hydroxy group in $R^3$ can be in the α- or β-position, free hydroxy groups being preferred.

Suitable as the ether and acyl residues are those known to persons skilled in the art. Readily cleavable ether residues are preferred, such as, for example, the tetrahydropyranyl, tetrahydrofuranyl, tert-butyldimethylsilyl, tert-butyldiphenylsilyl, tribenzylsilyl residues. Suitable acyl residues are, for example, acetyl, propionyl, butyryl, benzoyl.

Halogen in the definitions for $R^5$, $R^6$ and Y means fluorine, chlorine, bromine and iodine.

The residues "$C_1$–$C_{10}$-alkanoyl" or "$C_1$–$C_{10}$-alkanesulfonyl" for $R^7$ correspond to the aforementioned alkyl groups of the same length, the difference being that they are linked to a carboxy group. Preferred is $C_1$–$C_4$-alkanoyl or -alkanesulfonyl.

Inorganic and organic bases, as known to one skilled in the art for the formation of physiologically compatible salts, are suitable for salt formation with the free acids ($R^5$=H). Examples that can be cited are: alkali hydroxides, such as sodium or potassium hydroxide, alkaline earth hydroxides, such as calcium hydroxide, ammonia, amines, such as ethanolamine, diethanolamine, triethanolamine, N-methylglucamine, morphine, tris(hydroxymethyl) methylamine, etc.

Those compounds of Formula I are preferred wherein $R^1$ means the group $COOR^5$, $R^3$ means hydrogen or hydroxy, $R^5$ means hydrogen or methyl, $R^7$ means methanesulfonyl, p is 0 to 4, n is 0 or 1.

The compounds of Formula I according to this application can be prepared as described in detail below:

A.

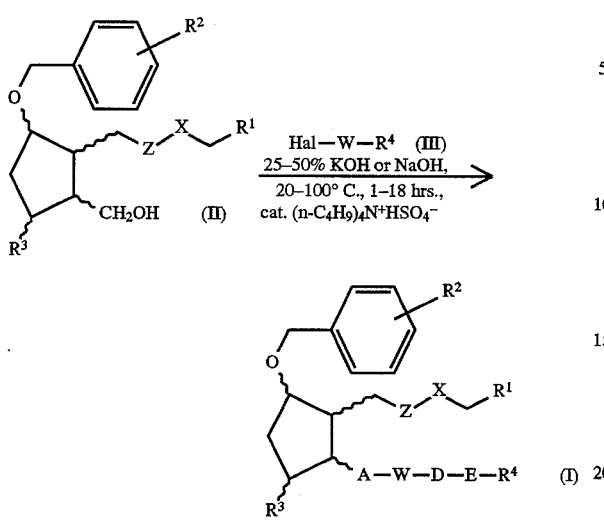

wherein
$R^1$, $R^2$, $R^3$, $R^4$, X, Z have the above-indicated meanings,
Hal is bromine or chlorine,
A,D,E mean a direct bond,
$R^1$ is —COOR$^5$ ester.

B.

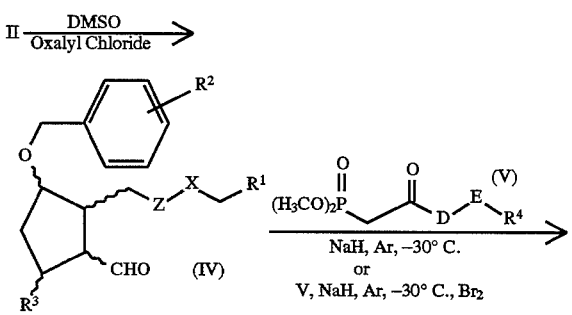

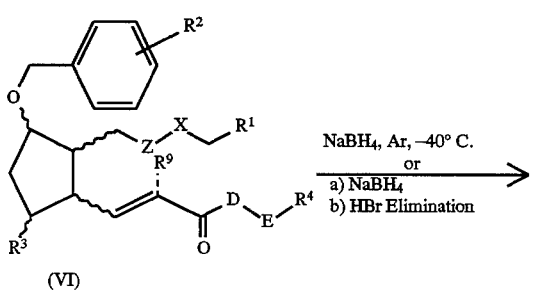

wherein
$R^2$, $R^3$, $R^4$, A, E, X, Z have the above-indicated meanings,

D means alkylene optionally substituted by alkyl,
$R^1$ means a —COOR$^5$ ester,
$R^9$ means hydrogen or bromine,
W means —CH(OH)—.

C.

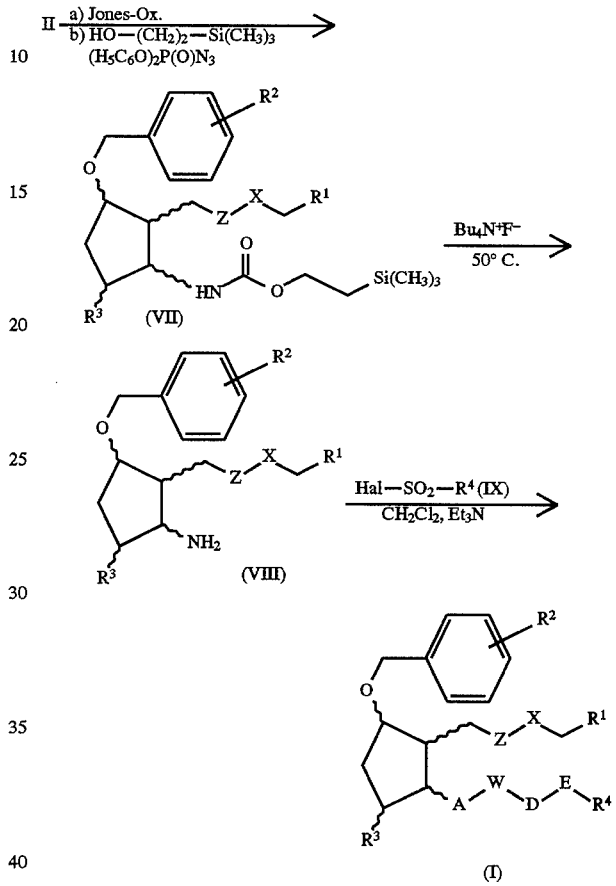

wherein
$R^2$, $R^3$, $R^4$, X, Z, Hal have the meanings given above,
A,W,D,E mean a direct bond,
$R^1$ means a —COOR$^5$ ester.

D.

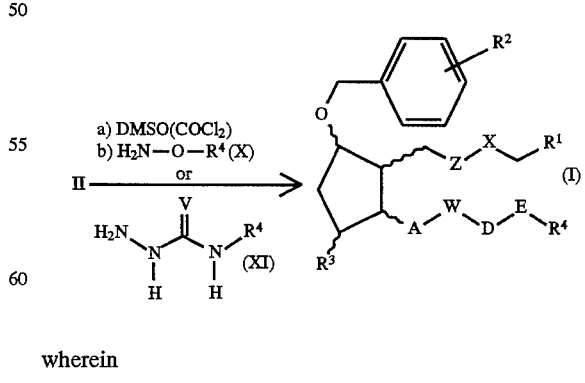

wherein
$R^2$, $R^3$, $R^4$, X, Z have the meanings given above,
A,W,E mean a direct bond,
$R^1$ means a —COOR$^5$ ester, D means

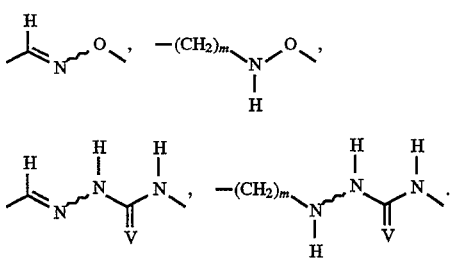

E.

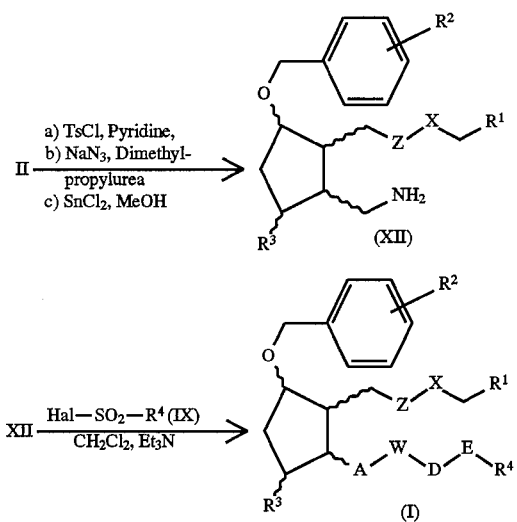

wherein

R$^1$, R$^2$, R$^3$, X, Z have the above-indicated meanings,

A,W,D,E mean a direct bond,

R$^1$ means a COOR$^5$ ester.

The compounds of Formula I can be prepared according to claim 3 in correspondence with the above-described process alternatives. The starting compounds of Formula II are produced corresponding to the directions indicated in Examples 2a–2e.

Saponification of the esters in —COOR$^5$ takes place, for example, with alkali or alkaline earth carbonates or hydroxides in an alcohol or in the aqueous solution of an alcohol. Suitable alcohols are aliphatic alcohols, such as, for example, methanol, ethanol, butanol, etc., but preferably methanol. Suitable alkali carbonates and hydroxides are lithium, sodium and potassium salts. The lithium and potassium salts are preferred. Suitable alkaline earth carbonates and hydroxides are, for example, calcium carbonate, calcium hydroxide, and barium carbonate. The reaction takes place generally at −10° C. to +70° C., but preferably at +25° C.

The reaction conditions of the subsequent process stages are:

(1) II→I (Process A)

In the presence of aqueous alkali or alkaline earth solutions and with the use of phase transfer catalysts (such as, for example, tetrabutylammonium hydrogen phosphate or sulfate), compounds of Formula II are reacted at 20°–100° C. within 1–16 hours with the reactant III as the organic phase or a solution of III in an inert, water-immiscible organic solvent.

(2) II→IV (Process B)

Oxidation of compounds of Formula II takes place according to known methods, such as, for example, according to the method of Swern, Collins, as well as with the use of pyridinium dichromate or chlorochromate in solvents such as dichloromethane, diethyl ether, tetrahydrofuran, benzene or toluene at −80° C. to −50° C. (Swern) or up to +30° C. (in case of the other oxidations) within 10 minutes to 8 hours.

IV→VI (Process B), VI→I (Process B)

The reaction of compounds IV with the phosphonates V, as well as the subsequent reduction or HBr elimination take place analogously to the conditions described in DOS 2,845, 770.

(3) II→VII (Process C)

The oxidation of the compounds of Formula II is preferably performed with Jones reagent or pyridinium chlorochromate, observing the reaction conditions required therefor. Subsequently, the rearrangement is conducted by heating with phosphoric acid diphenyl ester azide in an inert solvent, such as, for example, toluene. The rearrangement product is isolated, after adding 2-(trimethylsilyl)ethanol, as compounds of Formula VII which latter are reacted to compounds of Formula VIII as described in the associated examples.

(4) VIII→I (Process C)

The compounds of Formula VIII are reacted with the compounds of Formula IX as set forth in the examples recited therefor.

(5) II→I (Process D)

The reaction takes place in analogy to the process described in WO 90/02740 (Process C, page 16).

(6) II→I (Process E)

Reaction of the compounds of Formula II to compounds of Formula XII and further to compounds of Formula I takes place as in the examples recited for this purpose.

Liberation of the functionally modified hydroxy groups R$^2$, R$^3$, R$^4$ and W takes place in accordance with the methods known to one skilled in the art. For example, ether blocking groups are split off in an aqueous solution of an organic acid, such as, for example, acetic acid, propionic acid, citric acid, and others, or in an aqueous solution of an inorganic acid, such as, for example, hydrochloric acid, or, in case of tetrahydropyranyl ethers, with the use of pyridinium p-toluenesulfonate, preferably in alcohols as the solvent or with the use of anhydrous magnesium bromide, preferably in diethyl ether as the solvent.

To improve solubility, a water-miscible inert solvent is suitably added when using aqueous-acidic reaction conditions. Suitable have proved to be, for example, alcohols, such as methanol and ethanol, ethers, such as dimethoxyethane, dioxane and tetrahdyrofuran, wherein tetrahydrofuran is utilized with preference.

Splitting off of the silyl ether blocking groups takes place, for example, with tetrabutylammonium fluoride according to the methods known to one skilled in the art. Examples of suitable solvents are tetrahydrofuran, diethyl ether, dioxane, methylene chloride, etc. The splitting-off step is performed with preference at temperatures of between 20° C. and 20° C.

Saponification of the acyl groups and prostaglandin esters takes place according to the methods known to persons skilled in the art, such as, for example, with alkaline catalysts, e.g. with alkali or alkaline earth carbonates or hydroxides, in an alcohol or in the aqueous solution of an alcohol. Suitable alcohols are aliphatic alcohols, for example methanol, ethanol, butanol, etc., but preferably methanol.

Suitable alkali carbonates and hydroxides are lithium, sodium and potassium salts. The lithium and potassium salts are preferred. Alkaline earth carbonates and hydroxides that can be used are, for example, calcium carbonate, calcium hydroxide, and barium carbonate. The reaction takes place generally at −10° C. to +70° C., but preferably at +25° C.

Introduction of the ester group $CO_2R^5$ for $R^1$, or $CO_2R^6$ for Y, wherein $R^5$ or $R^6$ means an alkyl group of 1–10 carbon atoms, takes place according to the methods known to one skilled in the art. The carboxy compounds ($R^5$=H or $R^6$=H) are reacted, for example, with diazohydrocarbons in a conventional way. Esterification with diazohydrocarbons is effected, for example, by mixing a solution of the diazohydrocarbon in an inert solvent, preferably in diethyl ether, with the carboxy compound, dissolved in the same or in another, likewise inert solvent, such as methylene chloride, for example. After the reaction is finished within 1–60 minutes, the solvent is removed and the ester purified as usual. Diazoalkanes are either known or can be prepared according to conventional methods [Org. Reactions, 8 : 389–394 (1954)].

Introducing the ester group $CO_2R^5$ for $R^1$ or $CO_2R^6$ for Y wherein $R^5$ or $R^6$ represents a substituted or unsubstituted aryl group takes place according to the methods known to persons skilled in the art. For example, the 1-carboxy compounds are reacted with the corresponding arylhydroxy compounds with dicyclohexyl carbodiimide in the presence of a suitable base, such as, for example, pyridine, dimethylaminopyridine, triethylamine, in an inert solvent such as, e.g. methylene chloride, ethylene chloride, chloroform, ethyl acetate, tetrahydrofuran, but preferably with chloroform. The reaction is performed at temperatures of between −30° C. and +50° C., preferably at +10° C.

The prostaglandin derivatives of Formula I wherein $R^5$ or $R^6$ means a hydrogen atom can be converted into salts with suitable amounts of the corresponding inorganic bases under neutralization. For example, by dissolving the corresponding acids in water containing stoichiometric amounts of the base, the solid inorganic salt is obtained after evaporation of the water or after addition of a water-miscible solvent, e.g. alcohol or acetone.

The amine salts are prepared as usual. For this purpose, the acid is dissolved in a suitable solvent, e.g. ethanol, acetone, diethyl ether or benzene, and 1–5 equivalents of the respective amine are added to this solution. During this step, the salt is ordinarily obtained in the solid form or is isolated conventionally after evaporation of the solvent.

The functional modification of the free hydroxy groups takes place according to the methods known to one skilled in the art. For example, in order to introduce the ether blocking groups, the reaction is carried out with dihydropyran or methyl vinyl ether in methylene chloride or chloroform with the use of catalytic amounts of an acidic condensation agent such as, for example, p-toluenesulfonic acid. The respective enol ether is added in excess, preferably in 1.2 to 10 times the quantity theoretically required. The reaction takes place normally at −10° C. to +30° C. and is finished after 2–45 minutes.

In order to introduce the silyl ether blocking groups, the reaction is carried out, for example, with tert-butyldiphenylchlorosilane or tert-butyldimethylchlorosilane in dimethylformamide with the use of a base, e.g. imidazole. The respective silyl chloride is added in an excess, preferably in 1.05 to 4 times the theoretically needed quantity. The reaction takes place usually at 0° C. to 30° C. and is completed after 1–24 hours.

Introduction of the acyl blocking groups is achieved by reacting a compound of Formula I in a manner known per se with a carboxylic acid derivative, such as, for example, an acid chloride, acid anhydride, etc.

Cyclodextrin clathrates are obtained analogously to the directions in WO 87/05294.

Liposomes are prepared by following the production method described in "Pharmazie in unserer Zeit" [Pharmacy in Our Times], 11: 98 (1982)".

All stereoisomeric forms likewise pertain to the subject matter of the invention. The four compounds characterized by this "wave line" on the five-membered ring of Formula I do not represent mixtures but rather are to mean in each case a concrete optical form which can be of the R or S configuration.

Biological effects and range of application of the novel $TXA_2$ antagonists:

The compounds of this invention are suitable for the therapy of diseases of the cardiovascular system, of the stomach, the pancreas, the liver, and the kidneys. They have blood-pressure-lowering and bronchodilatory effects. They are excellently suited for inhibition of thrombocyte activation. Consequently, the novel $TXA_2$ antagonists of-Formula I represent valuable active pharmaceuticals. Moreover, the compounds are distinguished by a higher selectivity, a substantially longer period of efficacy, and a higher stability as compared with similar $TXA_2$ antagonists.

The novel $TXA_2$ antagonists possess the properties typical for this class of compounds, such as, for example, lowering of peripheral arterial, the coronary, and the pulmonary vascular resistance, lowering of pulmonary blood pressure, lowering of systemic blood pressure without simultaneously reducing the stroke volume and coronary blood flow, promotion of renal blood flow and blood circulation through other peripheral organs, raising of cerebral blood flow, inhibition of thrombocyte activation and dissolution of thrombi, inhibition of bronchoconstriction, inhibition of gastric acid secretion, cytoprotection of the heart, of the gastric and intestinal mucosa, of the liver, cytoprotection in the pancreas and in the kidneys, as well as antiallergic properties. For this reason, the novel $TXA_2$ antagonists are suitable, in principle, for the treatment of cerebral vascular accidents, for the prophylaxis and therapy of coronary heart disease, e.g. coronary thrombosis, for treatment of cardiac infarction, peripheral arterial diseases, for the prophylaxis and therapy in other thromboembolic diseases, and in case of arteriosclerosis, in ischemic attacks of the CNS system and other circulatory disorders of the brain, such as, for example, migraine, for the treatment of hypertension and for the treatment of diseases accompanied by an increase in pulmonary vascular resistance, such as, for example, pulmonary hypertension, and for therapy of shock, asthma, and allergic rhinitis. They can furthermore be utilized for inhibition of labor and for the treatment of gestational toxicoses.

The novel $TXA_2$ antagonists can additionally be used for improving organ function after transplants, for example in kidney transplants, for preventing rejection reactions, in place of heparin, or as an adjuvant in dialysis or hemofiltration, and in the preservation of blood plasma stores, e.g. of stored blood platelets.

The novel $TXA_2$ antagonists exhibit anti-inflammatory properties and are suitable, in principle, for the therapy of topical diseases, e.g. dermal ischemia or decubitus ulcers.

The novel $TXA_2$ antagonists possess anti-metastatic activity and antiproliferative properties. They are suitable, in principle, for the treatment of neoplasias. The novel $TXA_2$ antagonists can be used in combination with, for example, carbacyclins, prostacyclin and its analogs, 7-oxo-prostacyclins, prostaglandins and their derivatives, and 6-oxo-PGE$_1$- and 6-oxo-9-fluoro-prostaglandin derivatives, with TXA$_2$-synthetase inhibitors, with phosphodiesterase inhibitors, with antagonists and receptor antagonists of various thrombocyte stimulators (for example, ADP, thrombin, collagen, PAF, adrenaline, serotonin, fibrinogen), with calcium antagonists, with fibrinolytics and thrombolytics, e.g. t-PA, with heparin and other anticoagulants, with-cyclooxygenase inhibitors, e.g. acetylsalicylic acid, with inhibitors of the lipoxygenases, as well as antagonists of lipoxygenase products, with vasodilators, such as, for example, nitro compounds, with antihypertensives, e.g. β-blockers, or with diuretics. The compounds according to this invention can act not only as TXA$_2$ antagonists but also in bifunctional fashion, i.e. TXA$_2$-antagonistically and simultaneously PGI$_2$-agonistically. The dosage of the compounds is 0.1–500 mg/day, also in several partial doses, if administered to human patients. The unit dosage for the pharmaceutically acceptable vehicle amounts to 0.1–100 mg. For parenteral administration, sterile, injectable aqueous or oily solutions are utilized. For purposes of oral administration, suitable are, for example, tablets, dragees or capsules.

The invention accordingly also concerns medicinal agents based on the compounds of general Formula I and customary auxiliary agents and carriers.

The active agents of this invention are to serve, in conjunction with the auxiliary agents known and customary in galenic pharmacy, for example for the production of blood-pressure-lowering medicines.

The unit dosage range for the ampoule is 0.1–100 mg, for the tablet 0.1–100 mg.

EXAMPLE 1

7-[(1R,2S,5S)-2-(4-Phenylbenzyloxy)-5-(4-fluorophenylsulfonylamino)cyclopentyl]-5(Z)-heptenoic Acid A solution of 55 mg (97 μmol) of the compound prepared according to Example 2 in 1 ml of methanol is combined with 0.5 ml of an approximately 5% strength potassium hydroxide solution and agitated for 20 hours at 23° C. By adding saturated citric acid, the mixture is acidified, diluted with water and repeatedly extracted with ethyl acetate. The product is washed with water, saturated sodium chloride solution, and dried over magnesium sulfate. The residue obtained after filtration and solvent removal is purified by chromatography on about 25 g of silica gel with a gradient system of n-hexane and ethyl acetate, thus isolating 32.8 mg (59 μmol, 61%) of the title compound as a colorless oil.

IR (film): 3600–2400, 3280, 3030, 3010, 2940, 2870, 1710, 1590, 1495, 1450, 1405, 1330, 1290, 1165, 1155, 1090, 1025, 915, 840, 765, 700, 670, 570 and 550 cm$^{-1}$

EXAMPLE 2

7-[(1R,2S,5S)-2-(4-Phenylbenzyloxy)-5-(4-fluorophenylsulfonylamino)cyclopentyl]-5(Z)-heptenoic Acid Methyl Ester A solution of 100 mg (245 μmol) of the amine prepared according to Example 2a in 1.2 ml of anhydrous dichloromethane is combined at 0° C. with 49.5 mg of triethylamine, 52.3 mg of 4-fluorosulfonic acid chloride, and agitated for 16 hours at 23° C. under an atmosphere of dry argon. The mixture is diluted with ethyl acetate, washed with 1N hydrochloric acid, 5% strength sodium bicarbonate solution, water, saturated sodium chloride solution, and dried over magnesium sulfate. The residue obtained after filtration and solvent removal is purified by chromatography on about 20 g of silica gel, thus isolating 61 mg (108 μmol, 44%) of the title compound as a colorless oil.

IR (film): 3280, 3060, 3030, 3010, 2950, 2870, 1735, 1715, 1595, 1495, 1440, 1335, 1295, 1230, 1165, 1155, 1090, 915, 760, 700 and 670 cm$^{-1}$

EXAMPLE 2a

7-[(1R,2S,5S)-2-(4-Phenylbenzyloxy)-5-aminocyclopentyl] 5(Z)-heptenoic Acid Methyl Ester A solution of 1.23 g (2.23 mmol) of the compound prepared according to Example 2b is combined with 11 ml of a 1-molar solution of tetrabutylammonium fluoride in tetrahydrofuran and heated for 2.5 hours to 50° C. After cooling, the mixture is combined with diethyl ether, washed with water, saturated sodium chloride solution, and dried over magnesium sulfate. The residue obtained after filtration and solvent removal is further reacted without purification.

EXAMPLE 2b

7-[(1R,2S,5S)-2-(4-Phenylbenzylocy)-5-(trimethylsilylethoxycarbonylamino)cyclopentyl]-5(Z)-heptenoic Acid Methyl Ester A solution of 1.62 g (3.71 mmol) of the acid produced according to Example 2c in 3.7 ml of anhydrous toluene is combined, under an atmosphere of dry argon, with 372 mg of triethylamine, 1.02 g of phosphoric acid diphenyl ester azide and heated for 2.5 hours to 90° C. The mixture is combined with 930 mg of 2-(trimethylsilyl)ethanol and agitated for another 18 hours at 90° C. After cooling, the mixture is diluted with diethyl ether, washed with 10% strength sodium hydroxide solution, saturated sodium chloride solution, and dried over magnesium sulfate. The residue obtained after filtration and solvent removal is purified by chromatography on 80 g of silica gel with a gradient system of n-hexane and ethyl acetate, thus isolating 1.23 g (2.23 mmol, 60%) of the title compound as a colorless oil.

IR (film): 3340, 3060, 3030, 3010, 2950, 2900, 1740–1690, 1600, 1530, 1490, 1250, 1170, 1060, 960, 860, 835, 760 and 700 cm$^{-1}$

EXAMPLE 2c

7-[(1R,2S,5S)-2-(4-Phenylbenzyloxy)-5-hydroxycarbonylcyclopentyl]-5(Z)-heptenoic Acid Methyl Ester A solution of 2.0 g (4.73 mmol) of the alcohol prepared according to Example 2d in 58 ml of acetone is cooled to −40° C., combined with 2.84 ml of a standardized chromosulfuric acid solution (Jones reagent), stirred for 1.5 hours at −40° C. to −15° C., and excess oxidizing agent is decomposed by adding 7 ml of isopropanol. The mixture is diluted with water, extracted repeatedly with diethyl ether, the combined organic extracts are washed with water and saturated sodium chloride solution and dried over magnesium sulfate. The residue obtained after filtration and removal of solvent is purified by chromatography on about 150 g of coarse silica gel with a gradient system of n-hexane and ethyl acetate, thus isolating 1.62 g (3.71 mmol, 79%) of the title compound as a colorless oil.

IR (film): 3600–2400, 3030, 3010, 2950, 2860, 1735, 1700, 1605, 1485, 1435, 1340, 1310, 1240, 1165, 1075, 760 and 695 cm$^{-1}$

EXAMPLE 2d

7-[(1R,2S,5S)-2-(4-Phenylbenzyloxy)-5-hydroxymethylcyclopentyl]-5(Z)-heptenoic Acid Methyl Ester A solution of 6.1 g (9.23 mmol) of the compound produced according to Example 2e in 120 ml of anhydrous tetrahydrofuran is combined with 17 g of tetrabutylammonium fluoride and agitated for 17 hours at 23° C. under an atmosphere of dry argon. The mixture is combined with water, repeatedly extracted with di-ethyl ether, the combined organic extracts are washed with water and saturated sodium chloride solution, and dried over magnesium sulfate. The residue obtained after filtration and solvent removal is purified by chromatography on about 300 g of silica gel with a gradient system of n-hexane and ethyl acetate, thus isolating 2.07 g (4.90 mmol, 53%) of the title compound as a colorless oil.

IR (film): 3600–3200, 3060, 3030, 3000, 2940, 2860, 1735, 1600, 1485, 1435, 1340, 1310, 1245, 1210, 1165, 1075, 825, 760 and 695 $cm^{-1}$

EXAMPLE 2e

7-[(1R,2S,5S)-2-(4-Phenylbenzyloxy)-5-(tert-butyldiphenylsilyloxymethyl)cyclopentyl]-5(Z)-heptenoic Acid Methyl Ester 4.0 g (8.09 mmol) of 7-[(1R,2S,5S)-5(tert-butyldiphenylsilyloxymethyl)-2-hydroxucyclopentyl]-5(Z)-heptenoic acid methyl ester (see DE 40 24 347.8, Example 1i) is dissolved in 12 ml of toluene, combined with 5.0 g of 4-phenylbenzyl bromide, 8 ml of a 50% strength potassium hydroxide solution, 368 mg of tetrabutylammonium hydrogen sulfate, and agitated for 18 hours at 23° C. The mixture is acidified by adding citric acid, diluted with ethyl acetate, washed with saturated sodium chloride solution, and dried over magnesium sulfate. The residue obtained after filtration and solvent removal is purified by chromatography on about 160 g of silica gel with a gradient system of n-hexane and ethyl acetate, thus isolating 3.05 g (4.61 mmol, 57%) of the title compound as a colorless oil. IR (film): 3070, 3050, 3030, 3000, 2950, 2930, 2850, 1735, 1600, 1485, 1430, 1360, 1110, 1005, 825, 760, 740 and 700 $cm^{-1}$

EXAMPLE 3

7-[(1R,2S,5S)-2-(4-Phenylbenzyloxy)-5-phenylsulfonylaminocyclopentyl]-5(Z)-heptenoic Acid 55.5 mg (101 µmol) of the compound prepared in accordance with Example 4 is saponified analogously to Example 1, thus isolating after working up and purification 38.7 mg (73 µmol, 72%) of the title compound as a colorless oil.

IR (film): 3600–2400, 3270, 3060, 3030, 3010, 2940, 2870, 1705, 1605, 1490, 1450, 1325, 1160, 1095, 1075, 965, 830, 760, 725, 690, 590 and 565 $cm^{-1}$

EXAMPLE 4

7-[(1R,2S,5S)-2-(4-Phenylbenzyloxy)-5-phenylsulfonylaminocyclopentyl]-5(Z)-heptenoic Acid Methyl Ester 100 mg (245 µmol) of the amine produced according to Example 2a is reacted analogously to Example 2 with the use of benzenesulfonic acid chloride, thus isolating after working up and purification 85 mg (156 µmol, 63%) of the title compound as a colorless oil.

IR(film): 3280, 3060, 3030, 3010, 2950, 2870, 1735, 1600, 1490, 1445, 1330, 1160, 1095, 1070, 910, 760, 720 and 690 $cm^{-1}$

EXAMPLE 5

7-[(1R,2S,5S)-2-(4-Phenylbenzyloxy)-5-(4-methylphenylsulfonylamino)cyclopentyl]-5(Z)-heptenoic Acid 39.2 mg (69 µmol) of the compound prepared according to Example 6 is saponified in analogy to Example 1, thus isolating after working up and purification 15.4 mg (28 µmol, 40%) of the title compound as a colorless oil.

IR (film): 3600–2400, 2960, 2930, 2870, 1690, 1450, 1425, 1405, 1385, 1155, 1095, 1070, 900 and 760 $cm^{-1}$

EXAMPLE 6

7-[(1R,2S,5S)-2-(4-Phenylbenzyloxy)-5-(4-methylphenylsulfonylamino)cyclopentyl]-5(Z)-heptenoic Acid Methyl Ester 100 mg (245 µmol) of the amine prepared in accordance with Example 2a is reacted analogously to Example 2 with the use of 4-methylphenylsulfonic acid chloride, thus isolating after working up and purification 49 mg (87 µmol, 36%) of the title compound as a colorless oil.

IR (film): 3280, 2950, 2870, 1735, 1600, 1450, 1425, 1405, 1385, 1155, 1095, 1070, 900 and 760 $cm^{-1}$

EXAMPLE 7

7-[(1R,2S,5S)-2-(4-Phenylbenzyloxy)-5-(2,5-dichlorophenylsulfonylamino)cyclopentyl]-5(Z)-heptenoic Acid 43.8 mg (71 µmol) of the compound prepared according to Example 8 is saponified analogously to Example 1, thus isolating after working up and purification 31 mg (51 µmol, 73 % ) of the title compound as a colorless oil.

IR (film): 3600–2400, 3300, 3090, 3060, 3030, 3010, 2940, 2870, 1710, 1600, 1490, 1450, 1375, 1340, 1245, 1165, 1100, 1075, 1045, 920, 895, 825, 760, 700, 680, 600,585 and 515 $cm^{-1}$

EXAMPLE 8

7-[(1R,2S,5S)-2-(4-Phenylbenzyloxy)-5-(2,5-dichlorophenylsulfonylamino)cyclopentyl]-5(Z)-heptenoic Acid Methyl Ester 100 mg (245 µmol) of the amine prepared according to Example 2a is reacted analogously to Example 2 with the use of 2,5-dichlorophenylsulfonic acid chloride, thus isolating after working up and purification 83.5 mg (135 µmol, 55%) of the title compound as a colorless oil.

IR (film): 3300, 3090, 3070, 3030, 3010, 2950, 2870, 1735, 1715, 1600, 1490, 1450, 1375, 1340, 1245, 1220, 1165, 1100, 1075, 1040, 825, 765, 700 and 680 $cm^{-1}$

EXAMPLE 9

7-[(1R,2S,5S)-2-(4-Phenylbenzyloxy)-5-(quinon-8-ylsulfonylamino)cyclopentyl]-5(Z)-heptenoic Acid 35.3 mg (59 µmol) of the compound prepared according to Example 10 is saponified in analogy to Example 1, thus isolating after working up and purification 13.9 mg (24 µmol, 40%) of the title compound as a colorless oil.

IR (film): 3600–2400, 3260, 3060, 3030, 3010, 2940, 2870, 1735, 1705, 1615, 1595, 1565, 1490, 1435, 1330, 1240 , 1215, 1165 , 1145 , 1070, 900 , 835, 790, 760, 700, 675 and 605 $cm^{-1}$

EXAMPLE 10

7-[(1R,2S,5S)-2-(4-Phenylbenzyloxy)-5-(quinon-8-ylsulfonylamino)cyclopentyl]-5(Z)-heptenoic Acid Methyl Ester 100 mg (245 µmol) of the amine prepared in accordance with Example 2a is reacted analogously to Example 2 with the use of quinon-8-ylsulfonic acid chloride, thus isolating after working up and purification 35.3 mg (59 µmol, 24%) of the title compound as a colorless oil.

IR (film): 3270, 3060, 3030, 3010, 2940, 2870, 1735, 1610, 1595, 1565, 1490, 1435, 1330, 1240, 1215, 1165, 1145, 1070, 900, 835, 790, 760 and 700 $cm^{-1}$

EXAMPLE 11

7-[(1R,2S,5S)-2-(4-Phenylbenzyloxy)-5-(naphth-2-ylsulfonylamino)cyclopentyl]-5(Z)-heptenoic Acid 29.5 mg (49 μmol) of the compound prepared according to Example 12 is saponified in analogy to Example 1, thus isolating after working up and purification 18.2 mg (31 μmol, 64%) of the title compound as a colorless oil.

IR (film): 3600–2400, 3270, 3060, 3030, 3010, 2940, 2870, 1705, 1590, 1490, 1450, 1435, 1410, 1325, 1155, 1130, 1075, 910, 820, 760, 695, 660, 615, 565, 550 and 475 cm$^{-1}$

EXAMPLE 12

7-[(1R,2S,5S)-2-(4-Phenylbenzyloxy)-5-(naphth-2-ylsulfonylamino)cyclopentyl]-5(Z)-heptenoic Acid Methyl Ester 100 mg (245 μmol) of the amine prepared according to Example 2a is reacted analogously to Example 2 with the use of naphth-2-ylsulfonic acid chloride, thus isolating after working up and purification 41.8 mg (70 μmol, 29%) of the title compound as a colorless oil.

IR (film): 3290, 3060, 3030, 3010, 2940, 2870, 1735, 1590, 1490, 1450, 1435, 1410, 1325, 1155, 1130, 1075, 910, 820, 760 and 700 cm$^{-1}$

EXAMPLE 13

7-[(1R,2S,5S)-2-(4-Phenylbenzyloxy)-5-(4-fluorophenylsulfonylaminomethyl)cyclopentyl]-5(Z)-heptenoic Acid 50 mg (86 μmol) of the compound prepared according to Example 14 is saponified analogously to Example 1, thus isolating after working up and purification 37 mg (65 μmol, 76%) of the title compound as a colorless oil.

IR (film): 3680–2400, 3280, 2930, 1710, 1595, 1495, 1330, 1240, 1155, 1090, 840, 760, 700 and 550 cm$^{-1}$

EXAMPLE 14

7-[(1R,2S,5S)-2-(4-Phenylbenzyloxy)-5-(4-fluorophenylsulfonylaminomethyl)cyclopentyl]-5(Z)-heptenoic Acid Methyl Ester 139 mg (329 μmol) of the amine prepared according to Example 14a is reacted analogously to Example 2 with the use of 4-fluorophenylsulfonic acid chloride, thus isolating after working up and purification 50 mg (86 μmol, 26%) of the title compound as a colorless oil.

IR (film): 3280, 3060, 3030, 3010, 2950, 2860, 1735, 1595, 1490, 1435, 1410, 1335, 1290, 1235, 1165, 1155, 1090, 840, 760, 700 and 670 cm$^{-1}$

EXAMPLE 14a

7-[(1R,2S,5S)-2-(4-Phenylbenzyloxy)-5-aminomethylcyclopentyl]-5(Z)-heptenoic Acid Methyl Ester To a solution of 402 mg of tin chloride dihydrate in 6.5 ml of anhydrous methanol, a solution of 532 mg (1.19 mmol) of the compound prepared according to Example 14b in 6.5 ml of methanol is added dropwise, and the mixture is stirred for 29 hours at 23° C. The mixture is concentrated, the residue is combined with sodium carbonate solution, extracted repeatedly with ethyl acetate, the combined organic extracts are washed with saturated sodium chloride solution, and dried over magnesium sulfate. The residue obtained after filtration and solvent removal (419 mg) is further reacted without purification.

EXAMPLE 14b

7-[(1R,2S,5S)-2-(4-Phenylbenzyloxy)-5-azidomethylcyclopentyl]-5(Z)-heptenoic Acid Methyl Ester 760 mg (1.32 mmol) of the compound prepared according to Example 14c is dissolved in 11.5 ml of dimethylpropylurea, combined with 1.55 g of sodium azide, and agitated for 5.5 hours at 40° C. under an atmosphere of dry argon. The mixture is diluted with diethyl ether, washed repeatedly with water and saturated sodium chloride solution, and dried over sodium sulfate. The residue obtained after filtration and solvent removal is purified by chromatography, thus isolating 532 mg (1.19 mmol, 90%) of the title compound as a colorless oil.

IR (film): 3060, 3030, 3010, 2950, 2860, 2090, 1735, 1600, 1490, 1450, 1435, 1345, 1245, 1165, 1120, 1075, 825, 760 and 700 cm$^{-1}$

EXAMPLE 14c

7-[(1R,2S,5S)-2-(4-Phenylbenzyloxy)-5-(4-methylphenylsulfonyloxymethyl)cyclopentyl]-5(Z)-heptenoic Acid Methyl Ester A solution of 700 mg (1.66 mmol) of the compound prepared in accordance with Example 2d in 4.3 ml of anhydrous pyridine is combined with 677 mg of p-toluenesulfonic acid chloride and agitated for hours at 23° C. under an atmosphere of dry argon. The mixture is combined with water, diluted with ethyl acetate, washed with 10% strength sulfuric acid, then with saturated sodium bicarbonate solution, and dried over sodium sulfate. The residue obtained after filtration and solvent removal is purified by chromatography on silica gel with the use of a gradient system of n-hexane and ethyl acetate, thus isolating 760 mg (1.32 mmol, 80%) of the title compound as a colorless oil.

IR (film): 3060, 3030, 3010, 2950, 2870, 1735, 1600, 1490, 1450, 1335, 1360, 1245, 1190, 1175, 1095, 1080, 945, 830, 815, 760, 700 and 665 cm$^{-1}$

EXAMPLE 15

7-[(1R,2S,5S)-2-(4-Phenylbenzyloxy)-5-(4-methylphenylsulfonylaminomethyl)cyclopentyl]-5(Z)-heptenoic Acid 66 mg (115 μmol) of the compound produced according to Example 16 is saponified in analogy to Example 1, thus isolating after working up and purification 54 mg (95 μmol, 83%) of the title compound as a colorless oil.

IR (film): 3680–2400, 3280, 2930, 1710, 1600, 1490, 1325, 1160, 815, 760, 700, 660 and 550 cm$^{-1}$

EXAMPLE 16

7-[(1R,2S,5S)-2-(4-Phenylbenzyloxy)-5-(4-methylphenylsulfonylaminomethyl)cyclopentyl]-5(Z)-heptenoic Acid Methyl Ester 139 mg (329 μmol) of the amine prepared as per Example 14a is reacted in analogy to Example 2 using 4-methylphenylsulfonic acid chloride, thus isolating after working up and purification 72 mg (125 μmol, 38%) of the title compound as a colorless oil.

IR (film): 3280, 3060, 3030, 3010, 2950, 2870, 1735, 1600, 1490, 1435, 1330, 1160, 1090, 815, 760, 700 and 665 cm$^{-1}$

EXAMPLE 17

7-[(1R,2S,5S)-2-(4-Phenylbenzyloxy)-5-(2,5-dichlorophenylsulfonylaminomethyl)cyclopentyl]-5(Z)-heptenoic Acid 35 mg (56 μmol) of the compound prepared in accordance with Example 18 is saponified in analogy to Example, thus isolating after working up and purification 25 mg (41 μmol, 73%) of the title compound as a colorless oil.

IR (film): 3680–2400, 3300, 3080, 3000, 2920, 1710, 1490, 1450, 1340, 1165, 825, 760, 700 and 580 cm$^{-1}$

EXAMPLE 18

7-[(1R,2S,5S)-2-(4-Phenylbenzyloxy)-5-(2,5-dichlorophenylsulfonylaminomethyl)cyclopentyl]-5(Z)-heptenoic Acid Methyl Ester 139 mg (329 µmol) of the amine produced according to Example 14a is reacted in analogy to Example 2 with the use of 2,5-dichlorophenylsulfonic acid chloride, thus isolating after working up and purification 35 mg (56 µmol, 17%) of the title compound as a colorless oil.

IR (film): 3300, 3090, 3060, 3030, 3010, 2940, 2870, 1735, 1600, 1490, 1450, 1415, 1375, 1340, 1245, 1165, 1100, 1040, 825, 760, 700 and 680 cm$^{-1}$

EXAMPLE 19

7-[(1R,2S,5S)-2-(4-Phenylbenzyloxy)-5-(2,4-difluorophenylsulfonylamino)cyclopentyl]-5(Z)-heptenoic Acid 88 mg (151 µmol) of the compound produced according to Example 20 is saponified analogously to Example 1, thus isolating after working up and purification 36.1 mg (63 µmol, 32%) of the title compound as a colorless oil.

IR (liqu.cap.): 3600–3200, 2940, 1710, 1605, 1490, 1430, 1340, 1275, 1160, 970, 760 and 700 cm$^{-1}$

EXAMPLE 20

7-[(1R,2S,5S)-2-(4-Phenylbenzyloxy)-5-(2,4-difluorophenylsulfonylamino)cyclopentyl]-5(Z)-heptenoic Acid Methyl Ester 257 mg (653 µmol) of the amine produced in accordance with Example 2a is reacted analogously to Example 2 with the use of 2,4-difluorophenylsulfonic acid chloride, thus isolating after working up and purification 114 mg (200 µmol, 30%) of the title compound as a colorless oil.

IR (film): 3400–3140, 2950, 1730, 1605, 1485, 1340, 1165, 1075, 970 and 850 cm$^{-1}$

EXAMPLE 21

7-[(1R,2S,5S)-2-(4-Phenylbenzyloxy)-5-(4-bromophenylsulfonylamino)cyclopentyl]-5(Z)-heptenoic Acid 174 mg (278 µmol) of the compound produced as per Example 22 is saponified analogously to Example 1, thus isolating after working up and purification 99 mg (162 µmol, 58%) of the title compound as a colorless oil.

IR (film): 3700–3140, 2940, 1710, 1575, 1490, 1330, 1160, 1070, 1010, 825, 760, 740 and 700 cm$^{-1}$

EXAMPLE 22

7-[(1R,2S,5S)-2-(4-Phenylbenzyloxy)-5-(4-bromophenylsulfonylamino)cyclopentyl]-5(Z)-heptenoic Acid Methyl Ester 257 mg (653 µmol) of the amine produced in accordance with Example 2a is reacted in analogy to Example 2 with the use of 4-bromophenylsulfonic acid chloride, thus isolating after working up and purification 174 mg (278 µmol, 43%) of the title compound as a colorless oil.

IR (film): 3280, 2960, 1740, 1578, 1490, 1440, 1340, 1165, 1070, 1013, 830, 765, 745 and 705 cm$^{-1}$

EXAMPLE 23

7-[(1R,2S,5S)-2-(4-Phenylbenzyloxy)-5-(3,4-dibromophenylsulfonylamino)cyclopentyl]-5(Z)-heptenoic Acid 114 mg (162 µmol) of the compound prepared as per Example 24 is saponified analogously to Example 1, thus isolating after working up and purification 61 mg (91 µmol, 54%) of the title compound as a colorless oil.

IR (KBr): 3700–3100, 2930, 2860, 1705, 1630, 1445, 1330, 1110, 760, 700, 695 and 660 cm$^{-1}$

EXAMPLE 24

7-[(1R,2S,5S)-2-(4-Phenylbenzyloxy)-5-(3,4-dibromophenylsulfonylamino)cyclopentyl]-5(Z)-heptenoic Acid Methyl Ester 257 mg (653 µmol) of the amine produced in Example 2a is reacted analogously to Example 2, using 3,4-dibromophenylsulfonic acid chloride, thus isolating after working up and purification 114 mg (162 µmol, 26%) of the title compound as a colorless oil.

IR (film): 3280, 2950, 1730, 1487, 1445, 1340, 1165, 1075, 785, 760 and 700 cm$^{-1}$

EXAMPLE 25

7-[(1R,2S,4R,5R)-2-(4-Phenylbenzyloxy)-4-hydroxy-5-(3,4-dibromophenylsulfonylamino)cyclopentyl]-5(Z)-heptenoic Acid 95 mg (115 µmol) of the compound prepared according to Example 26 is saponified in analogy to Example 1, thus isolating after working up and purification 66 mg (95 µmol, 81%) of the title compound as a colorless oil.

IR (KBr): 3600–3360, 3360–3100, 2930, 1705, 1570, 1485, 1450, 1330, 1100, 915, 820, 760 and 700 cm$^{-1}$

EXAMPLE 26

7-[(1R,2S,4R,5R)-2-(4-Phenylbenzyloxy)-4-benzoyloxy-5-(3,4-dibromophenylsulfonylamino)cyclopentyl]-5(Z)-heptenoic Acid Methyl Ester 212 mg (412 µmol) of the amine prepared according to Example 26a is reacted in analogy to Example 2 with the use of 3,4-dibromophenylsulfonic acid chloride, thus isolating after working up and purification 95 mg (115 µmol, 32%) of the title compound as a colorless oil.

IR (film): 3400–3120, 2940, 1715, 1645, 1600, 1485, 1450, 1345, 1270, 1165, 1020, 930, 760, 715 and 700 cm$^{-1}$

EXAMPLE 26a

7-[(1R,2S,4R)-2-(4-Phenylbenzyloxy)-4-benzoyloxy-5-aminocyclopentyl]-5(Z)-heptenoic Acid Methyl Ester A solution of 1.34 g (1.99 mmol) of the compound produced according to Example 26b in THF is combined with 9 ml of a 1-molar solution of tetrabutylammonium fluoride in tetrahydrofuran and heated for 2.75 hours to 50° C. After cooling, the mixture is combined with diethyl ether, washed with water, saturated sodium chloride solution, and dried over magnesium sulfate. The residue obtained after filtration and solvent removal is further reacted without purification.

EXAMPLE 26b

7-[(1R,2S,4R,5R)-2-(4-Phenylbenzyloxy)-4-benzoyloxy-5(trimethylsilylethoxycarbonylamino)cyclopentyl]-5(Z)-heptenoic Acid Methyl Ester A solution of 1.62 g (3.04 mmol) of the acid produced according to Example 26c in 3 ml of anhydrous toluene is combined under an atmosphere of dry argon with 307 mg of triethylamine, 836 mg of phosphoric acid diphenyl ester azide, and the mixture is heated for 2 hours to 90° C., then combined with 754 mg of 2-(trimethylsilyl)ethanol and agitated for another 23 hours at 90° C. After cooling, the mixture is diluted with diethyl ether, washed with 10% strength sodium hydroxide solution, saturated sodium chloride solution, and dried over magnesium sulfate. The residue obtained after filtration and solvent removal is purified by chromatography on silica gel with a gradient system of n-hexane and ethyl acetate, thus isolating 1.34 g (1.99 mmol, 66%) of the title compound as a colorless oil.

IR (film): 3460–3200, 2950, 1720, 1535, 1455, 1275, 1250, 1120, 1070, 860, 840, 765 and 715 cm$^{-1}$

EXAMPLE 26c

7-[(1R,2S,4R,5R)-2-(4-Phenylbenzyloxy)-4-benzoyloxy-5hydroxycarbonylcyclopentyl]-5(Z)-heptenoic Acid Methyl Ester A solution of 2.42 g (4.46 mmol) of the alcohol prepared according to Example 26d in 55 ml of acetone is cooled to −46° C., combined with 2.67 ml of a standardized chromosulfuric acid solution (Jones reagent), agitated for 1.5 hours at −40° C. to −10° C., and excess oxidizing agent is decomposed by adding 6.6 ml of isopropanol. The mixture is diluted with water, extracted repeatedly with diethyl ether, the combined organic extracts are washed with water and saturated sodium chloride solution, and dried over magnesium sulfate. The residue obtained after filtration and solvent removal is purified by chromatography on silica gel with a gradient system of n-hexane and ethyl acetate, thus isolating 1.69 g (3.04 mmol, 68%) of the title compound as a colorless oil.

IR (film): 3680–2800, 1740–1710, 1605, 1490, 1450, 1275, 1115, 765 and 715 cm$^{-1}$

EXAMPLE 26d

7-[(1R,2S,4R,5S)-2-(4-Phenylbenzyloxy)-4-benzoyloxy-5-hydroxymethylcyclopentyl]-5(Z)-heptenoic Acid Methyl Ester 4.29 g (5.49 mmol) of 7-[(1R,2S,4R,5S)-2-(4-phenylbenzyloxy)-4-benzoyloxy-5-(tert-butyldiphenylsilyloxymethyl-)cyclopentyl]-5(Z)-heptenoic acid methyl ester [prepared according to M. Shibasaki et al. THL 25, 1067 (1984), Example 2e, J. S. Bindra, R. Bindra, Prostaglandin Synthesis, Academic Press 1977] dissolved in 70 ml of anhydrous tetrahydrofuran is combined with 8.7 g of tetrabutylammonium fluoride and agitated for 1.25 hours under an atmosphere of dry argon. The mixture is combined with water, extracted repeatedly with diethyl ether, the combined organic extracts are washed with water and saturated sodium chloride solution, and dried over magnesium sulfate. The residue obtained after filtration and solvent removal is purified by chromatography on silica gel with a gradient system of n-hexane and ethyl acetate, thus isolating 2.42 g (4.46 mmol, 81%) of the title compound as a colorless oil.

IR (film): 3640–3200, 2940, 1740–1715, 1605, 1490, 1450, 1315, 1275, 1120, 1070, 1025, 760 and 715 cm$^{-1}$

EXAMPLE 27

7-[(1R,2S,4R,5R)-2-(4-Phenylbenzyloxy)-4-hydroxy-5-(2,4-difluorophenylsulfonylamino)cyclopentyl]-5(Z)-heptenoic Acid 86 mg (121 μmol) of the compound prepared according to Example 28 is saponified in analogy to Example 1, thus isolating after working up and purification 44 mg (76 μmol, 62%) of the title compound as a colorless oil.

IR (KBr): 3520, 3280, 3025, 2930, 1725, 1600, 1490, 1425, 1340, 1165, 1075, 1020, 860, 760 and 700 cm$^{-1}$

EXAMPLE 28

7-[(1R,2S,4R,5R)-2-(4-Phenylbenzyloxy)-4-benzoyloxy-5-(2,4-difluorophenylsulfonylamino)cyclopentyl]-5(Z)-heptenoic Acid Methyl Ester 212 mg (412 μmol) of the amine produced according to Example 26a is reacted in analogy to Example 2 with the use of 2,4-difluorophenylsulfonic acid chloride, thus isolating after working up and purification 86 mg (121 μmol, 35%) of the title compound as a colorless oil.

IR (film): 3700–3130, 2940, 1715, 1605, 1490, 1450, 1345, 1275, 1165, 1120, 970, 855, 765 and 715 cm$^{-1}$

EXAMPLE 29

7-[(1R,2S,4R,5R)-2-(4-Phenylbenzyloxy)-4-hydroxy-5(4-fluorophenylsulfonylamino)cyclopentyl]-5(Z) heptenoic Acid 101 mg (147 μmol) of the compound prepared according to Example 30 is saponified analogously to Example 1, thus isolating after working up and purification 38 mg (67 μmol, 45%) of the title compound as a colorless oil.

IR (KBr): 3500, 3330, 2930, 1730, 1590, 1490, 1445, 1330, 1240, 1155, 1090, 840, 760 and 700 cm$^{-1}$

EXAMPLE 30

7-[(1R,2S,4R,5R)-2-(4-Phenylbenzyloxy)-4-benzoyloxy-5-(4-fluorophenylsulfonylamino)cyclopentyl]-5(Z)-heptenoic Acid Methyl Ester 212 mg (412 μmol) of the amine produced according to Example 26a is reacted in analogy to Example 2 with the use of 4-fluorophenylsulfonic acid chloride, thus isolating after working up and purification 101 mg (147 μmol, 42%) of the title compound as a 10 colorless oil.

IR (film): 3400–3120, 2940, 1715, 1595, 1495, 1450, 1340, 1270, 1155, 840, 765 and 715 cm$^{-1}$

EXAMPLE 31

7-[(1R,2S,4R,5R)-2-(4-Phenylbenzyloxy)-4-hydroxy-5-(4-methylphenylsulfonylamino)cyclopentyl]-5(Z)-heptenoic Acid 86 mg (126 μmol) of the compound produced in accordance with Example 32 is saponified in analogy to Example 1, thus isolating after working up and purification 21 mg (37 μmol, 29%) of the title compound as a colorless oil.

IR (KBr): 3600–2800, 3495, 3300, 2940, 1730, 1710, 1600, 1490, 1340, 1320, 1160, 1090, 920, 820, 760 and 700 cm$^{-1}$

EXAMPLE 32

7-[(1R,2S,4R,5R)-2-(4-Phenylbenzyloxy)-4-benzoyloxy-5-(4-methylphenylsulfonylamino)cyclopentyl]-5(Z)-heptenoic Acid Methyl Ester 212 mg (412 μmol) of the amine produced according to Example 26a is reacted analogously to Example 2, using 4-methylphenylsulfonic acid chloride, thus isolating after working up and purification 86 mg (126 μmol, 36%) of the title compound as a colorless 10 oil.

IR (film): 3400–3120, 2950, 1740–1710, 1605, 1490, 1450, 1270, 1160, 910, 815, 765 and 715 cm$^{-1}$

EXAMPLE 33

7-[(1R,2S,4R,5R)-2-(4-Phenylbenzyloxy)-4-hydroxy-5-(4-bromophenylsulfonylamino)cyclopentyl]-5(Z)-heptenoic Acid 53 mg (71 μmol) of the compound produced according to Example 34 is saponified in analogy to Example 1, thus isolating after working up and purification 23 mg (37 μmol, 52%) of the title compound as a colorless oil.

IR (KBr): 3600–2700, 3500, 3320, 2940, 1730, 1710, 1575, 1390, 1330, 1110, 1090, 1070, 920, 760, 740 and 700 cm$^{-1}$

EXAMPLE 34

7-[(1R,2S,4R,5R)-2-(4-Phenylbenzyloxy)-4-benzoyloxy-5-(4-bromophenylsulfonylamino)cyclopentyl]-5(Z)-heptenoic Acid Methyl Ester 212 mg (412 µmol) of the amine produced according to Example 26a is reacted analogously to Example 2 with the use of 4-bromophenylsulfonic acid chloride, thus isolating after working up and purification 53 mg (71 µmol, 20%) of the title compound as a colorless oil.

IR (film): 3400–3120, 2950, 1715, 1575, 1490, 1455, 1275, 1165, 1010, 825, 765, 740 and 715 cm$^{-1}$

EXAMPLE 35

6-[(1R,2S,5S)-2-(4-Phenylbenzyloxy)-5-(phenylsulfonylaminomethyl)cyclopentyl]-4 (Z)-hexeonoic Acid 93 mg (170 µmol) of the compound prepared according to Example 36 is saponified in analogy to Example 1, thus isolating after working up and purification 69 mg (130 µmol, 76%) of the title compound as a colorless oil.

IR (liqu. cap.): 3700–2700, 3280, 2920, 1710, 1490, 1450, 1330, 1160, 1090, 760 and 690 cm$^{-1}$

EXAMPLE 36

6-[(1R,2S,5S)-2-(4-Phenylbenzyloxy)-5-(phenylsulfonylaminomethyl)cyclopentyl]-4(Z)-hexenoic Acid Methyl Ester 193 mg (470 µmol) of the amine produced according to Example 36a is reacted analogously to Example 2 with the use of phenylsulfonic acid chloride, thus isolating after working up and purification 93 mg (170 µmol, 36%) of the title compound as a colorless oil.

IR (film): 3280, 2950, 1720, 1600, 1490, 1435, 1160, 1090, 765 and 700 cm$^{-1}$

EXAMPLE 36a

6-[(1R,2S,5S)-2-(4-Phenylbenzyloxy)-5-aminomethylcyclopentyl]-4(Z)-hexenoic Acid Methyl Ester A solution of 1.025 g (2.36 mmol) of the compound produced according to Example 36b in 7 ml of methanol is added dropwise to a solution of 798 mg of tin chloride dihydrate in 14 ml of anhydrous methanol, and the mixture is stirred for 18 hours at 23° C., then concentrated, the residue is combined with sodium carbonate solution, repeatedly extracted with ethyl acetate, the combined organic extracts are washed with saturated sodium chloride solution, and dried over magnesium sulfate. The residue (790 mg) obtained after filtration and solvent removal is further reacted without purification.

EXAMPLE 36b

6-[(1R,2S,5S)-2-(4-Phenylbenzyloxy)-5-azidomethylcyclopentyl]-4(Z)-hexenoic Acid Methyl Ester 1.38 mg (2.45 mmol) of the compound prepared according to Example 36c is dissolved in 14 ml of dimethylpropylurea, combined with 2.50 g of sodium azide, and agitated for 16 hours at 40° C. under an atmosphere of dry argon. The mixture is diluted with diethyl ether, washed repeatedly with water and saturated sodium chloride solution, and dried over magnesium sulfate. The residue obtained after filtration and solvent removal is purified by chromatography, thus isolating 1.025 g (2.36 mmol, 97%) of the title compound as a colorless oil.

IR (film): 2950, 2860, 2100, 1740, 1490, 1450, 1345, 1170, 1080, 760 and 700 cm$^{-1}$

EXAMPLE 36c

6-[(1R,2S,5S)-2-(4-Phenylbenzyloxy)-5-(4-methylphenylsulfonyloxymethyl)cyclopentyl]-4(Z)-hexenoic Acid Methyl Ester A solution of 2.1 g (5.14 mmol) of the compound prepared as per Example 36d in 13.3 ml of anhydrous pyridine is combined with 2.1 g of p-toluenesulfonic acid chloride and agitated for 16 hours at 23° C. under an atmosphere of dry argon. The mixture is combined with water, diluted with ethyl acetate, washed with 10% strength sulfuric acid, then with saturated sodium bicarbonate solution, and dried over sodium sulfate. The residue obtained after filtration and solvent removal is purified by chromatography on silica gel with the use of a gradient system of n-hexane and ethyl acetate, thus isolating 1.38 g (2.45 mmol, 48%) of the title compound as a colorless oil.

IR (film): 3060, 3030, 3005, 2945, 2870, 1735, 1605, 1490, 1450, 1360, 1245, 1190, 1175, 1095, 945, 825, 760 and 700 cm$^{-1}$

EXAMPLE 36d

6-[(1R,2S,5S)-2-(4-Phenylbenzyloxy)-5-hydroxymethylcyclopentyl]-4(Z)-hexenoic Acid Methyl Ester 12.9 g (20 mmol) of 6-[(1R,2S,5S)-2-(4-phenylbenzyloxy)-5-(tert-butyldiphenylsilyloxymethyl)cyclopentyl]-4(Z)-hexenoic acid methyl ester (see PCT/DE91/00604, Example 78g) is dissolved in 140 ml of anhydrous tetrahydrofuran, combined with 33.4 ml of a 1-molar tetrabutylammonium fluoride solution in tetrahydrofuran, and stirred for 16 hours at 23° C. under an atmosphere of dry argon. The mixture is combined with water, extracted repeatedly with diethyl ether, the combined organic extracts are washed with water and saturated sodium chloride solution, and dried over magnesium sulfate. The residue obtained after filtration and solvent removal is purified by chromatography with a gradient system of n-hexane and ethyl acetate, thus isolating 7.25 g (17.7 mmol, 89%) of the title compound as a colorless oil.

IR (liqu. cap.): 3700–3120, 3000, 2960, 2870, 1740, 1490, 1440, 1345, 1170, 1080, 760 and 700 cm$^{-1}$

EXAMPLE 37

6-[(1R,2S,5S)-2-(4-Phenylbenzyloxy)-5-(4-methylphenylsulfonylaminomethyl)cyclopentyl]-4(Z)-hexenoic Acid 126 mg (220 µmol) of the compound prepared in accordance with Example 38 is saponified analogously to Example 1, thus isolating after working up and purification 88 mg (163 µmol, 72%) of the title compound as a colorless oil IR (liqu. cap.): 3420–2800, 3280, 2930, 1710, 1600, 1490, 1330, 1160, 1090, 815, 760 and 700 cm$^{-1}$

EXAMPLE 38

6-[(1R,2 S,5S)-2-(4-Phenylbenzyloxy)-5-(4-methylphenylsulfonylaminomethyl)cyclopentyl]-4(Z)-hexenoic Acid Methyl Ester 193 mg (470 µmol) of the amine prepared as per Example 36a is reacted analogously to Example 2 with the use of 4-methylphenylsulfonyl chloride, thus isolating after working up and purification 126 mg (220 µmol, 48%) of the title compound as a colorless oil.

IR (film): 3280, 3060, 3025, 2950, 1730, 1600, 1490, 1435, 1360, 1330, 1190, 1080, 830, 760 and 700 cm$^{-1}$

EXAMPLE 39

6-[(1R,2S,5S)-2-(4-Phenylbenzyloxy)-5-(4-fluorophenylsulfonylaminomethyl)cyclopentyl]-4(Z)-hexenoic Acid 115 mg (200 µmol) of the compound prepared according to Example 40 is saponified in analogy to Example 1, thus isolating after working up and purification 84 mg (152 µmol, 74%) of the title compound as a colorless oil.

IR (liqu. cap.): 3600–2700,3280, 2920, 1710, 1590, 1490, 1330, 1150, 1090, 840, 760 and 700 cm$^{-1}$

EXAMPLE 40

6-[(1R,2S,5S)-2-(4-Phenylbenzyloxy)-5-(4-fluorophenylsulfonylaminomethyl)cyclopentyl]-4(Z)-hexenoic Acid Methyl Ester 193 mg (470 μmol) of the amine produced according to Example 36a is reacted in analogy to Example 2 with the use of 4-fluorophenylsulfonyl chloride, thus isolating after working up and purification 115 mg (200 μmol, 43%) of the title compound as a colorless oil.

IR (film): 3280, 3060, 3025, 2950, 1730, 1595, 1490, 1435, 1335, 1290, 1235, 1160, 1090, 760 and 700 cm$^{-1}$

EXAMPLE 41

6-[(1R,2S,5S)-2-(4-Phenylbenzyloxy)-5-(2,4-difluorophenylsulfonylaminomethyl)cyclopentyl]-4(Z)-hexenoic Acid 144 mg (250 μmol) of the compound prepared according to Example 42 is saponified analogously to Example 1, thus isolating after working up and purification 76 mg (133 μmol, 54%) of the title compound as a colorless oil.

IR (liqu. cap.): 3700–2700, 3300, 2920, 1710, 1600, 1485, 1430, 1340, 1275, 1170, 1075, 970, 850, 760 and 700 cm$^{-1}$

EXAMPLE 42

6-[(1R,2S,5S)-2-(4-Phenylbenzyloxy)-5-(2,4-difluorophenylsulfonylaminomethyl)cyclopentyl]-4(Z)-hexenoic Acid Methyl Ester 193 mg (470 μmol) of the amine produced according to Example 36a is reacted in analogy to Example 2 with the use of 2,4-difluorophenylsulfonyl chloride, thus isolating after working up and purification 144 mg (250 μmol, 52%) of the title compound as a colorless oil.

IR (film): 3280, 3030, 2940, 1730, 1600, 1490, 1425, 1345, 1170, 1075, 1030, 860, 760 and 700 cm$^{-1}$

EXAMPLE 43

6-[(1R,2S,5S)-2-(4-Phenylbenzyloxy)-5-(4-bromophenylsulfonylamino)cyclopentyl]-4(Z)-hexenoic Acid 213 mg (350 μmol) of the compound prepared according to Example 44 is saponified analogously to Example 1, thus isolating after working up and purification 178 mg (296 μmol, 86%) of the title compound as a colorless oil.

IR (KBr): 3600–2400, 3440, 3220, 2920, 2900, 1700, 1580, 1390, 1155, 1070, 820, 760 and 740 cm$^{-1}$

EXAMPLE 44

6-[(1R,2S,5S)-2-(4-Phenylbenzyloxy)-5-(4-bromophenylsulfonylamino)cyclopentyl]-4(Z)-hexenoic Acid Methyl Ester 182 mg (460 μmol) of the amine produced in accordance with Example 44 a is reacted analogously to Example 2, using 4-bromophenylsulfonyl chloride, thus isolating after working up and purification 213 mg (350 μmol, 76%) of the title compound as a colorless oil.

IR (film): 3280, 2955, 1735, 1575, 1490, 1440, 1330, 1160, 1070, 830, 765 and 700 cm$^{-1}$

EXAMPLE 44a

6-[(1R,2S,5S)-2-(4-Phenylbenzyloxy)-5-aminocyclopentyl]-4(Z)-hexenoic Acid Methyl Ester A solution of 2.1 g (3.91 mmol) of the compound prepared according to Example 44b in tetrahydrofuran is combined with 18 ml of a 1-molar solution of tetrabutylammonium fluoride in tetrahydrofuran and heated for 3 hours to 50° C. After cooling, the mixture is combined with methyl tertbutyl ether, washed with water, saturated sodium chloride solution, and dried over magnesium sulfate. The residue obtained after filtration and solvent removal is further reacted without purification.

EXAMPLE 44b

6-[(1R,2S,5S)-2-(4-Phenylbenzyloxy)-5-(trimethylsilylethoxycarbonylamino)cyclopentyl]-4(Z)-hexenoic Acid Methyl Ester A solution of 2.4 g (5.7 mmol) of the acid prepared according to Example 44c in 5.6 ml of anhydrous toluene is combined under an atmosphere of dry argon with 0.78 ml of triethylamine, 1.22 ml of phosphoric acid diphenyl ester azide, and the mixture is heated for 2 hours to 90° C. The mixture is combined with 1.7 ml of 2-(trimethylsilyl)ethanol and agitated for another 22 hours at 90° C. After cooling, the mixture is diluted with methyl tert-butyl ether, washed with 10% strength sodium hydroxide solution, saturated sodium chloride solution, and dried over magnesium sulfate. The residue obtained after filtration and solvent removal is purified by chromatography on silica gel with a gradient system of n-hexane and ethyl acetate, thus isolating 2.10 g (3.91 mmol, 69%) of the title compound as a yellowish oil.

IR (film): 3340, 3060, 2955, 2900, 1740, 1690, 1530, 1490, 1250, 1060, 860, 760 and 700 cm$^{-1}$

EXAMPLE 44c

6-[(1R,2S,5S)-2-(4-Phenylbenzyloxy)-5-hydroxycarbonylcyclopentyl]-4(Z)-hexenoic Acid Methyl Ester A solution of 1.81 g (4.42 mmol) of the alcohol produced as per Example 36d in 50 ml of acetone is cooled to –40° C., combined with 2.66 ml of a standardized chromosulfuric acid solution (Jones reagent), stirred for 2 hours at –40° C. to –15° C., and excess oxidizing agent is decomposed by adding isopropanol. The mixture is diluted with water, extracted repeatedly with diethyl ether, the combined organic extracts are washed with water and saturated sodium chloride solution, and dried over magnesium sulfate. The residue obtained after filtration and solvent removal is purified by chromatography on coarse silica gel with a gradient system of n-hexane and ethyl acetate, thus isolating 1.14 g (2.7 mmol, 61%) of the title compound as a yellowish oil.

IR (film): 3600–2500, 1735, 1700, 1600, 1485, 1340, 1300, 1235, 760 and 700 cm$^{-1}$

EXAMPLE 45

6-[(1R,2S,5S)-2-(4-Phenylbenzyloxy)-5-(4-trifluoromethylphenylsulfonylamino)cyclopentyl]-4(Z)-hexenoic Acid 90 mg (150 μmol) of the compound produced according to Example 46 is saponified in analogy to Example 1, thus isolating after working up and purification 63 mg (110 μmol, 73%) of the title compound as a colorless oil.

IR (KBr): 3600–2400, 3440, 3280, 2920, 1710, 1410, 1330, 1160, 1070 and 715 cm$^{-1}$

EXAMPLE 46

6-[(1R,2S,5S)-2-(4-Phenylbenzyloxy)-5-(4-trifluoromethylphenylsulfonylamino)cyclopentyl]-4(Z)-hexenoic Acid Methyl Ester 182 mg (460 μmol) of the amine produced according to Example 44 a is reacted analogously to Example 2 with the use of 4-trifluoromethylphenylsulfonyl chloride, thus isolat-

EXAMPLE 47

6-[(1R,2S,5S)-2-(4-Phenylbenzyloxy)-5-(2,4-difluorophenylsulfonylamino)cyclopentyl]-4(Z)-hexenoic Acid 1.55 mg (270 μmol) of the compound produced as per Example 48 is saponified in analogy to Example 1, thus isolating after working up and purification 138 mg (250 μmol, 92%) of the title compound as a colorless oil.

IR (liqu. cap.): 3720–2400, 3280, 2930, 1710, 1600, 1490, 1340, 1160, 1070, 970, 760 and 700 $cm^{-1}$

EXAMPLE 48

6-[(1R,2S,5S)-2-(4-Phenylbenzyloxy)-5-(2,4-difluorophenylsulfonylamino)cyclopentyl]-4(Z)-hexenoic Acid Methyl Ester 182 mg (460 μmol) of the amine prepared according to Example 44 a is reacted in analogy to Example 2 with the use of 2,4-difluorophenylsulfonyl chloride, thus isolating after working up and purification 155 mg (270 μmol, 59%) of the title compound as a colorless oil.

IR (film): 3280, 3025, 2920, 1735, 1595, 1490, 1345, 1170, 1030, 860 and 760 $cm^{-1}$

EXAMPLE 49

6-[(1R,2S,5S)-2-(4-Phenylbenzyloxy)-5-(4-fluorophenylsulfonylamino)cyclopentyl]-4(Z)-hexenoic Acid 133 mg (240 μmol) of the compound produced according to Example 50 is saponified in analogy to Example 1, thus isolating after working up and purification 128 mg (239 μmol, 98%) of the title compound as a colorless oil.

IR (liqu. cap.): 3600–2800, 3280, 2930, 1710, 1590, 1490, 1330, 1240, 1150, 840, 760 and 700 $cm^{-1}$

EXAMPLE 50

6-[(1R,2S,5S)-2-(4-Phenylbenzyloxy)-5-(4-fluorophenylsulfonylamino)cyclopentyl]-4(Z)-hexenoic Acid Methyl Ester 182 mg (460 μmol) of the amine prepared as per Example 44a is reacted analogously to Example 2 with the use of 4-fluorophenylsulfonyl chloride, thus isolating after working up and purification 133 mg (240 μmol, 52%) of the title compound as a colorless oil.

IR (film): 3280, 3055, 3010, 2940, 1735, 1595, 1490, 1435, 1230, 1165, 1090, 760 and 700 $cm^{-1}$

EXAMPLE 51

6-[(1R,2S,5S)-2-(4-Phenylbenzyloxy)-5-(4-methylphenylsulfonylamino)cyclopentyl]-4(Z)-hexenoic Acid 131 mg (238 μmol) of the compound prepared according to Example 52 is saponified in analogy to Example 1, thus isolating after working up and purification 29 mg (53 μmol, 22%) of the title compound as a colorless oil.

IR (liqu. cap.): 3600–2800, 3280, 2930, 1710, 1490, 1425, 1330, 1155 and 760 $cm^{-1}$

EXAMPLE 52

6-[(1R,2S,5S)-2-(4-Phenylbenzyloxy)-5-(4-methylphenylsulfonylamino)cyclopentyl]-4(Z)-hexenoic Acid Methyl Ester 182 mg (460 μmol) of the amine produced according to Example 44a is reacted analogously to Example 2 with the use of 4-methylphenylsulfonyl chloride, thus isolating after working up and purification 131 mg (238 μmol, 51%) of the title compound as a colorless oil.

IR (film): 3280, 2940, 1735, 1590, 1450, 1425, 1380, 1155, 1095, 900, 760 and 700 $cm^{-1}$

EXAMPLE 53

6-(1R,2S,5S)-2-(4-Phenylbenzyloxy)-5-(phenylsulfonylamino)cyclopentyl]-4(Z)-hexenoic Acid 156 mg (290 μmol) of the compound produced in accordance with Example 54 is saponified in analogy to Example 1, thus isolating after working up and purification 96 mg (184 μmol, 63%) of the title compound as a colorless oil.

IR (liqu. cap.): 3680–2400, 3290, 2920, 2850, 1710, 1490, 1450, 1330, 1160, 1070, 910, 760 and 700 $cm^{-1}$

EXAMPLE 54

6-[(1R,2S,5S)-2-(4-Phenylbenzyloxy)-5-(phenylsulfonylamino)cyclopentyl]-4(Z)-hexenoic Acid Methyl Ester 182 mg (460 μmol) of the amine prepared as per Example 44a is reacted analogously to Example 2 with the use of phenylsulfonyl chloride, thus isolating after working up and purification 156 mg (290 μmol, 63%) of the title compound as a colorless oil.

IR (film): 3280, 2950, 1730, 1600, 1455, 1425, 1155, 1070, 900 and 760 $cm^{-1}$

EXAMPLE 55

7-[(1R,2S,4R,5S)-2-(4-Phenylbenzyloxy)-4-hydroxy-5-(diphenylmethoxyiminomethyl)cyclopentyl]-5(Z)-heptenoic Acid 88.1 mg (142 μmol) of the compound prepared according to Example 56 is saponified in analogy to Example 1, thus isolating after working up and purification 45.8 mg (75 μmol, 53%) of the title compound.

IR (liqu. cap.): 3700–2400, 3030, 2930, 1705, 1600, 1485, 1450, 1420, 1345, 1125, 1075, 1020, 920, 760 and 700 $cm^{-1}$

EXAMPLE 56

7-[(1R,2S,4R,5S)-2-(4-Phenylbenzyloxy)-4-hydroxy-5-(diphenylmethoxyiminomethyl)cyclopentyl]-5(Z)-heptenoic Acid Methyl Ester 132.2 mg (188 μmol) of the compound produced according to Example 57 is dissolved in 1.5 ml of absolute ethanol, combined with 4.8 mg of pyridinium p-toluenesulfonate, and agitated for 3 hours at 50° C. The solvent is removed and the residue is purified by chromatography, thus isolating 88.1 mg (142 μmol, 76%) of the desired compound as a colorless oil.

IR (film): 3700–3160, 3040, 2940, 1740, 1605, 1495, 1455, 1350, 1130, 1080, 765 and 700 $cm^{-1}$

EXAMPLE 57

7-[(1R,2S,4R,5S)-2-(4-Phenylbenzyloxy)-4-(tetrahydropyranyloxy)-5-(diphenylmethoxyiminomethyl)cyclopentyl]-5(Z)-heptenoic Acid Methyl Ester 120 mg (230 μmol) of the compound prepared as per Example 57a is dissolved in 1.7 ml of absolute ethanol, combined with 124.1 mg (623 μmol) of hydroxylamine diphenyl methyl ether, a few drops of pyridine, and agitated for 20 hours at room temperature. The mixture is concentrated, diluted with ethyl acetate, washed repeatedly with saturated sodium chloride solution, and dried over sodium sulfate. The residue obtained after filtration and solvent removal is purified by chromatography, thus isolating 132.2 mg (188 mol, 82%) of the desired compound as a colorless oil.

IR (film): 3070, 2940, 1740, 1605, 1490, 1405, 1345, 1245, 1130, 1080, 1025, 920, 765 and 700 cm$^{-1}$

EXAMPLE 57a

7-[(1R,2S,4R,5S)-2-(4-Phenylbenzyloxy)-4-(tetrahydropyranyloxy)-5-formylcyclopentyl]-5(Z)-heptenoic Acid Methyl Ester 399 mg (3.143 mmol) of oxalyl chloride, diluted with 3.9 ml of absolute methylene chloride, is cooled to −60° C. under argon. To this solution is added dropwise 549 mg (6.464 mmol) of dimethyl sulfoxide in 3.9 ml of absolute methylene chloride within 10 minutes, and the mixture is then stirred for 10 minutes. A solution of 1 g (1.921 mmol) of the compound produced according to Example 57b in 3.9 ml of absolute methylene chloride is added dropwise within 10 minutes to this mixture and agitated for 1.25 hours at -60° C. The batch is combined at −30° C. with 689 mg (6.808 mmol) of triethylamine, allowed to warm up to room temperature, and stirred for 15 minutes. The reaction mixture is diluted with 200 ml of ether and 10 ml of water, washed repeatedly with saturated sodium chloride solution, and dried over sodium sulfate. The residue obtained after filtration and solvent removal is further reacted without purification.

EXAMPLE 57b

7-[(1R,2S,4R,5S)-2-(4-Phenylbenzyloxy)-4-(tetrahydropyranyloxy)-5-(hydroxymethyl)cyclopentyl]-5(Z)-heptenoic Acid Methyl Ester A solution of 9.31 g (17.8 mmol) of 7-[(1R,2S,4R,5S)-2-(4-phenylbenzyloxy)-4-(tetrahydropyranyloxy)-5-(tert-butyldiphenylsilyloxymethyl)cyclopentyl]-5(Z)-heptenoic acid methyl ester (M. Shibasaki et al., THL 25, 1067 [1984], Example 2e, J. S. Bindra, R. Bindra, Prostaglandin Synthesis, Academic Press, 1977) in 235 ml of anhydrous tetrahydrofuran is combined with 16.8 g of tetrabutylammonium fluoride and agitated for 15.5 hours at 23° C. under an atmosphere of dry argon. The mixture is combined with water, extracted repeatedly with diethyl ether, the combined organic extracts are washed with water and saturated sodium chloride solution, and dried over magnesium sulfate. The residue obtained after filtration and solvent removal is purified by chromatography on about 400 g of silica gel with a gradient system of n-hexane and ethyl acetate, thus isolating 3.71 g (7.1 mmol, 49%) of the title compound 5 as a colorless oil.

IR (film): 3600–3200, 3020, 2940, 1735, 1600, 1490, 1315, 1245, 1070, 760 and 700 cm$^{-1}$

EXAMPLE 58

7-[(1R,2S,4R,5S)-2-(4-Phenylbenzyloxy)-4-hydroxy-5-(4-fluorobenzyloxyiminomethyl)cyclopentyl]-5(Z)-heptenoic Acid 75 mg (134 μmol) of the compound produced according to Example 59 is saponified in analogy to Example 1, thus isolating after working up and purification 44.2 mg (79 μmol, 61%) of the title compound.

IR (liqu. cap.): 3600–2500, 2830, 1705, 1600, 1510, 1490, 1410, 1345, 1225, 1155, 1075, 1040, 825, 760 and 700 cm$^{-1}$

EXAMPLE 59

7-[(R1,2S,4R,5S)-2-(4-Phenylbenzyloxy)-4-hydroxy-5-(4-fluorobenzyloxyiminomethyl)cyclopentyl]-5(Z)-heptenoic Acid Methyl Ester 125.5 mg (194 mol) of the compound prepared according to Example 60 is reacted analogously to Example 56, thus isolating after working up and purification 75 mg (134 μmol, 69%) of the title compound as a colorless oil.

IR (film): 3700–3140, 3010, 2940, 2870, 1735, 1605, 1510, 1440, 1350, 1225, 835, 765 and 700 cm$^{-1}$

EXAMPLE 60

7-[(R1,2S,4R,5S)-2-(4-Phenylbenzyloxy)-4-(tetrahydropyranyloxy)-5-(4-fluorobenzyloxyiminomethyl)cyclopentyl]-5(Z)-heptenoic Acid Methyl Ester 120 mg (230 μmol) of the compound produced according to Example 57a is reacted analogously to Example 57, using hydroxylamine-4-fluorobenzyl ether, thus isolating after working up and purification 125.3 mg (194 μmol, 84%) of the desired compound as a colorless oil.

IR (film): 2940, 2870, 1740, 1605, 1510, 1440, 1225, 1155, 1130, 1030, 825, 765 and 700 cm$^{-1}$

EXAMPLE 61

7-[(1R,2S,4R,5S)-2-(4-Phenylbenzyloxy)-4-hydroxy-5-(cyclohexylmethoxyiminomethyl)cyclopentyl]-5(Z)-heptenoic Acid 60.1 mg (109 μmol) of the compound prepared according to Example 62 is saponified in analogy to Example 1, thus isolating after working up and purification 43.5 mg (81 μmol, 74%) of the title compound.

IR (liqu. cap.): 3700–2400, 2920, 2850, 1710, 1490, 1450, 1410, 1345, 1125, 1080, 1035, 760 and 700 cm$^{-1}$

EXAMPLE 62

7-[(1R,2S,4R,5S)-2-(4-Phenylbenzyloxy)-4-hydroxy-5-(cyclohexylmethoxyiminomethyl)cyclopentyl]-5(Z)-heptenoic Acid Methyl Ester 115.6 mg (183 mol) of the compound produced according to Example 60 is reacted in analogy to Example 56, thus isolating after working up and purification 60.1 mg (109 μmol, 59%) of the title compound as a colorless oil.

IR (film): 3700–3200, 2930, 2860, 1740, 1490, 1455, 1350, 1220, 1175, 1080, 1040, 765 and 700 cm$^{-1}$

EXAMPLE 63

7-[(1R,2S,4R,5S)-2-(4-Phenylbenzyloxy)-4-(tetrahydropyranyloxy)-5-(cyclohexylmethoxyiminimethyl )cyclopentyl]-5(Z)-heptenoic Acid Methyl Ester 120 mg (230 μmol) of the compound prepared according to Example 57a is reacted analogously to Example 57 with the use of hydroxylamine (cyclohexylmethyl) ether, thus isolating after working up and purification 124.6 mg (196 μmol, 86%) of the desired compound as a colorless oil.

IR (film): 2930, 2855, 1740, 1450, 1350, 1130, 1080, 1030, 765 and 700 cm$^{-1}$

EXAMPLE 64

7-[(1R,2S,4R,5S)-2-(4-Phenylbenzyloxy)-4-hydroxy-5-(benzyloxyiminomethyl)cyclopentyl]-5(Z)-heptenoic Acid 65.6 mg (121 μmol) of the compound produced according to Example 65 is saponified in analogy to Example 1, thus isolating after working up and purification 50.3 mg (96 μmol, 79%) of the title compound.

IR (liqu. cap.): 3700–2400, 3030, 2930, 1705, 1490, 1455, 1410, 1395, 1125, 1075, 1040, 915, 760, 735 and 700 cm$^{-1}$

EXAMPLE 65

7-[(1R,2S,4R,5S)-2-(4-Phenylbenzyloxy)-4-hydroxy-5-(benzyloxyiminomethyl)cyclopentyl]-5(Z)-heptenoic Acid Methyl Ester 108.3 mg (173 mol) of the compound produced according to Example 66 is reacted analogously to Example 56, thus isolating after working up and purification 65.6 mg (121 µmol, 70%) of the title compound as a colorless oil.

IR (film): 3700–3140, 3030, 2935, 2885, 1735, 1490, 1455, 1440, 1350, 1215, 1125, 1075, 760 and 700 cm$^{-1}$

EXAMPLE 66

7-[(1R,2S,4R,5S)-2-(4-Phenylbenzyloxy)-4-(tetrahydropyranyloxy)-5-(benzyloxyiminomethyl)cyclopentyl]-5(Z)-heptenoic Acid Methyl Ester 100 mg (191 µmol) of the compound prepared as per Example 57a is reacted analogously to Example 57 with the use of hydroxylamine benzyl ether, thus isolating after working up and purification 108.3 mg (173 µmol, 90%) of the desired compound as a colorless oil.

IR (film): 2940, 2870, 1740, 1605, 1510, 1440, 1350, 1225, 1030, 835, 765 and 700 cm$^{-1}$

EXAMPLE 67

7-[(1R,2S,4R,5S)-2-(4-Phenylbenzyloxy)-4-hydroxy-5-(4-trifluoromethylbenzyloxyiminomethyl)cyclopentyl]-5(Z)-heptenoic Acid 61.3 mg (100 µmol) of the compound prepared according to Example 68 is saponified in analogy to Example 1, thus isolating after working up and purification 46.4 mg (78 µmol, 78%) of the title compound.

IR (liqu. cap.): 3700–2400, 2930, 1710, 1490, 1415, 1325, 1165, 1125, 1065, 1030, 825, 760 and 700 cm$^{-1}$

EXAMPLE 68

7-[(1R,2S,4R,5S)-2-(4-Phenylbenzyloxy)-4-hydroxy-5-(4-trifluoro,ethylbenzyloxyiminomethyl)cyclopentyl]-5(Z)-heptenoic Acid Methyl Ester 108.5 mg (156 mol) of the compound produced according to Example 69 is reacted in analogy to Example 56, thus isolating after working up and purification 61.3 mg (100 µmol, 64.3%) of the title compound as a colorless oil.

IR (film): 3700–3200, 3010, 2940, 2870, 1735, 1605, 1510, 1490, 1350, 1225, 1010, 825,765 and 700 cm$^{-1}$

EXAMPLE 69

7-[(1R,2S,4R,5S)-2-(4-Phenylbenzyloxy)-4-(tetrahydropyranyloxy)-5-(4-trifluoromethylbenzyloxyiminomethyl)cyclopentyl]-5(Z)-heptenoic Acid Methyl Ester 100 mg (191 µmol) of the compound prepared according to Example 57a is reacted analogously to Example 57 with the use of hydroxylamine 4-trifluoromethylbenzyl ether, thus isolating after working up and purification 108.5 mg (156 µmol, 81%) of the desired compound as a colorless oil.

IR (film): 2940, 2870, 1740, 1620, 1490, 1440, 1325, 1165, 1125, 1065, 820, 765 and 700 cm$^{-1}$

EXAMPLE 70

7-[(1R,2S,4R,5S)-2-(4-Phenylbenzyloxy)-4-hydroxy-5-(1-naphthylmethoxyiminomethyl)cyclopentyl]-5(Z)-heptenoic Acid 84.7 mg (143 µmol) of the compound produced as per Example 71 is saponified in analogy to Example 1, thus isolating after working up and purification 57.7 mg (100 µmol, 70%) of the title compound.

IR (liqu. cap.): 3700–2400, 3400, 3070, 3030, 3010, 1705, 1600, 1510, 1490, 1410, 1385, 1345, 1235, 1125, 1070, 915, 760 and 700 cm$^{-1}$

EXAMPLE 71

7-[(1R,2S,4R,5S)-2-(4-Phenylbenzyloxy)-4-hydroxy-5-(1-naphthylmethoxyiminomethyl)cyclopentyl]-5(Z)-heptenoic Acid Methyl Ester 124.1 mg (189 mol) of the compound produced as per Example 72 is reacted analogously to Example 56, thus isolating after working up and purification 84.7 mg (143 µmol, 78%) of the title compound as a colorless oil.

IR (film): 3660–3120, 3010, 2935, 2870, 1735, 1600, 1515, 1490, 1435, 1375, 1345, 1220, 1170, 1080, 1010, 800, 795, 780, 760 and 700 cm$^{-1}$

EXAMPLE 72

7-[(1R,2S,4R,5S)-2-(4-Phenylbenzyloxy)-4-(tetrahydropyranyloxy)-5-(1-naphthylmethoxyiminomethyl)cyclopentyl]-5(Z)-heptenoic Acid Methyl Ester 100 mg (191 µmol) of the compound produced according to Example 57a is reacted in analogy to Example 57 with the use of hydroxylamine 1-(naphthylmethyl) ether, thus isolating after working up and purification 124.1 mg (183 µmol, 96%) of the desired compound as a colorless oil.

IR (film): 2940, 2870, 1640, 1605, 1510, 1440, 1350, 1235, 1040, 835, 765 and 700 cm$^{-1}$

EXAMPLE 73

7-[(1R,2S,4R,5S)-2-(4-Phenylbenzyloxy)-4-hydroxy-5-(ω-phenylsemicarbazonomethyl)cyclopentyl]-5(Z)-heptenoic Acid 48.2 mg (85 µmol) of the compound prepared in accordance with Example 74 is saponified in analogy to Example 1, thus isolating after working up and purification 26.5 mg (48 µmol, 56%) of the title compound.

IR (liqu. cap.): 3700–2400, 3370, 2930, 1710–1630, 1590, 1540, 1450, 1235, 1135, 1100, 1075, 760 and 695 cm$^{-1}$

EXAMPLE 74

7-[(1R,2S,4R,5S)-2-(4-Phenylbenzyloxy)-4-hydroxy-5-(ω-phenylsemicarbazonomethyl)cyclopentyl]-5(Z)-heptenoic Acid Methyl Ester 101.4mg (155 µmol) of the compound prepared as per Example 75 is dissolved in 3 ml of a mixture of glacial acetic acid, water and tetrahydrofuran, and the mixture is agitated for 22 hours at room temperature. The solvent is removed, the residue is combined four times with toluene and in each case evaporated to dryness. After chromatography, 65.5 mg (115 µmol, 74%) of the desired compound is obtained as a colorless oil.

IR (film): 3700–2700, 3380, 2940, 1735, 1680–1660, 1595, 1535, 1500, 1315, 1230, 1125, 760 and 695 cm$^{-1}$

EXAMPLE 75

7-[(1R,2S,4R,5S)-2-(4-Phenylbenzyloxy)-4-(tetrahydropyranyloxy)-5-(ω-phenylsemicarbazonomethyl)cyclopentyl]-5(Z)-heptenoic Acid Methyl Ester 200 mg (384 µmol) of the compound prepared according to Example 57a is reacted in analogy to Example 57 with the use of ω-phenylsemicarbazide, thus isolating after working up and purification 187.7 mg (287 µmol, 75%) of the desired compound as a colorless oil.

IR (film): 3600–2800, 3380, 3210, 2950, 1740, 1695, 1600, 1535, 1500, 1360, 1320, 1225, 1135, 1035, 1025, 760 and 700 cm$^{-1}$

EXAMPLE 76

(8R,9S,11R,12R,15S)-9-(4-Phenylbenzyloxy)-11,15-dihydroxy-5(Z),13(E)-prostatadienoic Acid 24.6 mg (46 µmol) of the compound produced according to Example 77 is saponified in analogy to Example 1, thus isolating after working up and purification 23.4 mg (45 µmol, 98%) of the title compound as a colorless oil.

IR (liqu. cap.): 3700–2300, 2930, 2860, 1710, 1490, 1410, 1345, 1240, 1175, 970, 760 and 700 cm$^{-1}$

EXAMPLE 77

(8R,9S,11R,12R,15S)-9-(4-Phenylbenzyloxy)-11,15-dihydroxy-5(Z),13(E)-prostadienoic Acid Methyl Ester 83.8 mg (135 mol) of the compound prepared according to Example 78 (II, polar spot) is reacted in analogy to Example 56, thus isolating after working up and purification 24.6 mg (46 μmol, 34%) of the title compound as a colorless oil.

IR (film): 3700–3100, 2930, 2860, 1740, 1490, 1435, 1345, 1075, 970, 760 and 700 cm$^{-1}$

EXAMPLE 78

(8R,9S,11R,12R,15R)-9-(4-Phenylbenzyloxy)-11-(tetrahydropyranyloxy)-15-hydroxy-5(Z),13 (E)-prostadienoic Acid Methyl Ester (I) and (8R,9S,11R,12R,15S)-9-(4-Phenylbenzyloxy)-11-(tetrahydropyranyloxy)-15-hydroxy-5(Z),13(E)-prostadienoic Acid Methyl Ester (II)

1.15 g (1,858 mmol) of the compound prepared as per Example 79 is dissolved in 21 ml of anhydrous methanol, cooled to −40° C., and combined in portions with 444 mg (11,728 mmol) of sodium borohydride. The mixture is stirred at −40° C. for another 50 minutes, 0.94 ml of glacial acetic acid is added dropwise, and the methanol is removed. The residue is taken up in methylene chloride, washed with saturated sodium chloride solution, and dried over sodium sulfate. The residue obtained after filtration and removal of solvent is purified by chromatography, thus isolating 468.9 mg (758 μmol, 41%) of the title compound I (nonpolar spot) and 424.6 mg (687 μmol, 37%) of the title compound II (polar spot) as colorless oils.

IR (film), I: 3700–3120, 2940, 2865, 1740, 1490, 1440, 1350, 1135, 1075, 1030, 975, 760 and 700 cm$^{-1}$ IR (film), II: 3700–3160, 2935, 2860, 1740, 1490, 1440, 1350, 1205, 1135, 1025, 975, 765 and 700 cm$^{-1}$

EXAMPLE 79

(8R,9S,11R,12R)-9-(4-Phenylbenzyloxy)-11-(tetrahydropyranyloxy)-15-oxo-5(Z),13-(E)-prostadienoic Acid Methyl Ester At room temperature under an argon atmosphere 979.5 mg (4.408 mmol) of (2-oxoheptyl)phosphonic acid dimethyl ester, dissolved in 13 ml of dimethoxyethane, is added dropwise to a suspension of 210 mg (4.371 mmol) of 50% sodium hydride in 25 ml of dimethoxyethane. To this mixture is added 187.5 mg (4.408 mmol) of dried lithium chloride and the mixture is stirred for one hour at room temperature. After cooling the suspension to −20° C., 2 g (3.841 mmol) of the compound produced according to Example 57a, dissolved in dimethoxyethane, is added dropwise thereto, and then the mixture is stirred for 2 hours at −20° C. and for 21 hours at room temperature, then cooled to −10° C., 0.44 ml of glacial acetic acid is added dropwise, the mixture is diluted with water and repeatedly extracted with ether. The organic phases are washed several times with 4% strength sodium bicarbonate solution and saturated sodium chloride solution. The residue obtained after filtration and solvent removal is purified by chromatography, thus isolating 1.16 g (1.86 mmol, 49%) of the title compound as a colorless oil.

IR (film): 2940, 2870, 1740, 1695, 1630, 1490, 1440, 1350, 1205, 1135, 1035, 765 and 700 cm$^{-1}$

EXAMPLE 80

(8R,9S,11R,12R,15R)-9-(4-Phenylbenzyloxy)-11,15-dihydroxy-5(Z),13(E)-prostadienoic Acid 14 mg (26 μmol) of the compound prepared as per Example 81 is saponified in analogy to Example 1, thus isolating after working up and purification 13.3 mg (25 μmol, 98%) of the title compound as a colorless oil.

IR (film): 3700–3200, 3500, 3360, 2930, 2860, 1710, 1675, 1490, 1410, 1345, 1270, 1050, 760 and 700 cm$^{-1}$

EXAMPLE 81

(8R,9S,11R,12R,15R)-9-(4-Phenylbenzyloxy)-11,15-dihydroxy-5(Z),13(E)-prostadienoic Acid Methyl Ester 86.4 mg (139 μmol) of the compound prepared according to Example 78 (I, nonpolar spot) is reacted analogously to Example 56, thus isolating after working up and purification 14 mg (26 μmol, 19%) of the title compound as a colorless oil.

IR (film): 3700–3100, 2925, 2860, 1740, 1485, 1435, 1340, 1075, 970, 760 and 700 cm$^{-1}$

EXAMPLE 82

(8R,9S,12R,15S)-9-(4-Phenylbenzyloxy)-15-hydroxy-5(Z),13(E)-prostadienoic Acid 58.2 mg (77 μmol) of the compound prepared according to Example 83 is dissolved in 2 ml of anhydrous tetrahydrofuran, combined with 292 mg of tetrabutylammonium fluoride, and agitated for 17 hours at room temperature. After dilution with ether, the product is washed with saturated sodium chloride solution, dried over sodium sulfate, filtered, and the solvent removed by a rotary evaporator. The product is purified by chromatography on silica gel, thus isolating 14.4 mg (28 μmol, 37%) of the title compound as a colorless oil.

IR (liqu. cap.): 3700–2300, 2930, 2860, 1710, 1490, 1455, 1410, 1340, 1240, 1075, 970,760 and 700 cm$^{-1}$

EXAMPLE 83

(8R,9S,12R,15S)-9-(4-Phenylbenzyloxy)-15-(tert-butyldiphenylsilyloxy)-5(Z),13(E)-prostadienoic Acid Methyl Ester 74.1 mg (80 μmol) of the compound produced according to Example 84 is dissolved in 0.7 ml of dimethoxyethane, combined with 53.5 mg of zinc dust, 62.1 mg of sodium iodide, and 0.04 ml of water, and heated for 16.5 hours under reflux. The reaction mixture is filtered, diluted with ether, shaken with dilute sodium thiosulfate solution and saturated sodium chloride solution. The residue obtained after drying over sodium sulfate, filtration and solvent removal is chromatographed on silica gel, thus isolating 58.3 mg (77 μmol, 96%) of the title compound as a colorless oil.

IR (film): 2960, 2940, 2860, 1740, 1490, 1430, 1235, 1110, 1070, 825, 760 and 700 cm$^{-1}$

EXAMPLE 84

(8R,9S,11R,12R,15S)-9-(4-Phenylbenzyloxy)-11-(4-methylphenylsulfonyloxy)-15-(tert-butyldiphenylsilyloxy)-5(Z),13(E)-prostadienoic Acid Methyl Ester 241 mg (312 μmol) of the compound prepared according to Example 85 is reacted in analogy to Example 14c, thus isolating after working up and purification 138.5 mg (149 μmol, 48%) of the title compound as a colorless oil.

IR (film): 2930, 2860, 1740, 1600, 1430, 1360, 1175, 1010, 925, 825, 765 and 700 cm$^{-1}$

EXAMPLE 85

(8R,9S,11R,12R,15S)-9-(4-Phenylbenzyloxy)-11-hydroxy-15-(tert-butyldiphenylsilyloxy)-5(Z),13(E)-prostadienoic Acid Methyl Ester 425.3 mg (496 mol) of the compound produced as per Example 86 is reacted analogously to Example 56, thus isolating after working up and purification 241 mg (312 µmol, 63%) of the title compound as a colorless oil.

IR (film): 3700–3180, 2930, 2860, 1740, 1595, 1425, 1360, 1015, 825, 760 and 700 cm$^{-1}$

EXAMPLE 86

(8R,9S,11R,12R,15S)-9-(4-Phenylbenzyloxy)-11-(tetrahydropyranyloxy)-15-(tert-butyldiphenylsilyloxy)-5(Z),13(E)-prostadienoic Acid Methyl Ester 329.1 mg (532 µmol) of the compound prepared according to Example 78 (II, polar spot) is dissolved in 2.1 ml of anhydrous dimethylformamide, combined with 0.351 ml (1.349 µmol) of tert-butyldiphenylsilyl chloride and 181 mg (2.660 mmol) of imidazole, and agitated for 2.5 hours at room temperature. The mixture is diluted with ether, washed repeatedly with saturated sodium bicarbonate solution and saturated sodium chloride solution, dried over magnesium sulfate, and the solvent is evaporated. After chromatography on silica gel, 439.1 mg (512 µmol, 96%) of the title compound is isolated as a colorless oil.

IR (film): 2940, 2855, 1740, 1600, 1430, 1360, 1010, 760 and 700 cm$^{-1}$

EXAMPLE 87

(8R,9S,12R,15R)-9-(4-Phenylbenzyloxy)-15-hydroxy-5(Z),13(E)-prostadienoic Acid 63.2 mg (83 µmol) of the compound prepared as per Example 88 is reacted in analogy to Example 82, thus isolating after working up and purification 13.4 mg (26 mol, 32%) of the title compound as a colorless oil.

IR (liqu. cap.): 3600–2400, 2930, 2860, 1710, 1490, 2460, 1410, 1390, 1240, 1135, 1070, 970, 760 and 700 cm$^{-1}$

EXAMPLE 88

(8R,9S,12R,15R)-9-(4-Phenylbenzyloxy)-15-(tert-butyldiphenylsilyloxy)-5(Z),13(E)-prostadienoic Acid Methyl Ester 80.4 mg (86 µmol) of the compound prepared according to Example 89 is reacted in analogy to Example 83, thus isolating after working up and purification 63.2 mg (83 mol, 96%) of the title compound as a colorless oil.

IR (film): 2960, 2935, 2860, 1740, 1490, 1465, 1430, 1245, 1110, 1075, 825, 760, 740 and 700 cm$^{-1}$

EXAMPLE 89

(8R,9S,11R,12R,15R)-9-(4-Phenylbenzyloxy)-11-(4-methylphenylsulfonyloxy)-15-(tert-butyldiphenylsilyloxy)-5(Z),13(E)-prostadienoic Acid Methyl Ester 206.4 mg (267 µmol) of the compound prepared according to Example 90 is reacted in analogy to Example 14c, thus isolating after working up and purification 139.9 mg (148 µmol, 57%) of the title compound as a colorless oil.

IR (film): 2935, 2860, 1740, 1595, 1430, 1360, 1175, 1010, 925, 825, 765 and 700 cm$^{-1}$

EXAMPLE 90

(8R,9S,11R,12R,15R)-9-(4-Phenylbenzyloxy)-11-hydroxy-15-(tert-butyldiphenylsilyloxy)-5(Z),13(E)-prostadienoic Acid Methyl Ester 490.7 mg (572 µmol) of the compound prepared according to Example 91 is reacted analogously to Example 56, thus isolating after working up and purification 206.4 mg (267 µmol, 47%) of the title compound as a colorless oil.

IR (film): 3700–3200, 2925, 2860, 1735, 1595, 1360, 1015, 825, 760 and 700 cm$^{-1}$

EXAMPLE 91

(8R,9S,11R,12R,15R)-9-(4-Phenylbenzyloxy)-11-(tetrahydropyranyloxy)-15-(tert-butyldiphenylsilyloxy)-5(Z),13(E)-prostadienoic Acid Methyl Ester 370 mg (598 µmol) of the compound prepared according to Example 78 (I, nonpolar spot) is reacted analogously to Example 68, thus isolating after working up and purification 501.9 mg (585 µmol, 98%) of the title compound as a colorless oil.

IR (film): 3000, 2930, 2860, 1740, 1490, 1430, 1350, 1010, 1075, 1020, 975, 820, 760, 740 and 700 cm$^{-1}$

EXAMPLE 92

(8R,9S,11R,12R,15S)-9-(4-Phenylbenzyloxy)-11,15-dihydroxy-15-cyclohexyl-16,17,18,19,20-pentanor-5(Z),13(E)-prostadienoic Acid 43.1 mg (79 µmol) of the compound prepared as per Example 93 is saponified in analogy to Example 1, thus isolating after working up and purification 31.6 mg (59 µmol, 75%) of the title compound as a colorless oil.

IR (liqu. cap.): 3700–2300, 2920, 2850, 1710, 1490, 1450, 1410, 1345, 1075, 1010, 970, 760 and 700 cm$^{-1}$

EXAMPLE 93

(8R,9S,11R,12R,15S)-9-(4-Phenylbenzyloxy)-11,15-dihydroxy-15-cyclohexyl-16,17,18,19,20-pentanor-5(Z),13(E)-prostadienoic Acid Methyl Ester 82.3 mg (130 mol) of the compound prepared according to Example 94 (II, polar spot) is reacted in analogy to Example 56, thus isolating after working up and purification 43.1 mg (79 µmol, 60%) of the title compound as a colorless oil.

IR (film): 3700–3100, 2830, 2750, 1740, 1490, 1450, 1345, 1215, 1170, 1075, 1010, 975, 760 and 700 cm$^{-1}$

EXAMPLE 94

(8R,9S,11R,12R,15R)-9-(4-Phenylbenzyloxy)-11-tetrahydropyranyloxy-15-hydroxy-15-cyclohexyl-16,17,18,19,20-pentanor-5(Z),13(E)-prostadienoic -Acid Methyl Ester (I) and (8R,9S,11R,12R,15S )-9-(4-Phenylbenzyloxy)-11-tetrahydropyranyloxy-15-hydroxy-15-cyclohexyl-16,17,18,19,20-pentanor-5(Z),13(E)-prostadienoic Acid Methyl Ester (II)

1.467 g (2.332 mmol) of the compound produced according to Example 95 is reacted analogously to Example 78, thus isolating 487.2 mg (773 µmol, 33%) of title compound I (nonpolar spot) and 461.5 mg (732 µmol, 32%) of title compound II (polar spot).

IR (film), I: 3700–3200, 2930, 2860, 1740, 1490, 1450, 1350, 1245, 1200, 1135, 1075, 1025, 975, 765 and 700 cm$^{-1}$

EXAMPLE 95

(8R,9S,11R,12R)-9-(4-Phenylbenzyloxy)-11-(tetrahydropyranyloxy)-15-oxo-15-cyclohexyl-16,17,18,19,20-pentanor-5(Z),13(E)-prostadienoic Acid Methyl Ester 2 g (3.841 mmol) of the compound prepared as per Example 57a is reacted analogously to Example 79, thus isolating after working up and purification 1.467 g (2.332 mol, 61%) of the title compound as a colorless oil.

IR (film): 2940, 2860, 1740, 1695, 1670, 1630, 1450, 1350, 1250, 1205, 1135, 1080, 1035, 765 and 700 cm$^{-1}$

EXAMPLE 96

(8R,9S,11R,12R,15R)-9-(4-Phenylbenzyloxy)-11,15-dihydroxy-15-cyclohexyl-16,17,18,19,20-pentanor-5(Z),13(E)-prostadienoic Acid 27.5 mg (50 µmol) of the compound prepared as per Example 97 is saponified in analogy to Example 1, thus isolating after working up and purification 26.1 mg (490 µmol, 97%) of the title compound as a colorless oil.

IR (liqu. cap.): 3700–2200, 2920, 2850, 1720, 1490, 1450, 1410, 1345, 1250, 1075, 1020, 760 and 700 cm$^{-1}$

EXAMPLE 97

(8R,9S,11R,12R,15R)-9-(4-Phenylbenzyloxy)-11,15-dihydroxy-15-cyclohexyl-16,17,18,19,20-pentanor-5(Z),13(E)-prostadienoic Acid Methyl Ester 84.5 mg (134 mol) of the compound prepared according to Example 94(I, nonpolar spot) is reacted in analogy to Example 56, thus isolating after working up and purification 27.5 mg (50 µmol, 38%) of the title compound as a colorless oil.

IR (film): 3680–3100, 2825, 2750, 1740, 1490, 1445, 1345, 1215, 1070, 975, 760 and 700 cm$^{-1}$

EXAMPLE 98

(8R,9S,11S,12R,15S)-9-(4-Phenylbenzyloxy)-11,15-dihydroxy-15-cyclohexyl-16,17,18,19,20-pentanor-5(Z),13(E)-prostadienoic Acid 45.5 mg (83 µmol) of the compound prepared according to Example 99 is saponified analogously to Example 1, thus isolating after working up 35.2 mg (66 µmol, 79%) of the title compound as a colorless oil.

IR (liqu. cap.): 3700–2300, 2920, 2850, 1710, 1490, 1450, 1240, 1060, 760 and 700 cm$^{-1}$

EXAMPLE 99

(8R,9S,11S,12R,15S)-9-(4-Phenylbenzyloxy)-11,15-dihydroxy-15-cyclohexyl-16,17,18,19,20-pentanor-5(Z),13(E)-prostadienoic Acid Methyl Ester 105.6 mg (134 mol) of the compound prepared according to Example 100 is reacted in analogy to Example 57b, thus isolating after working up and purification 45.5 mg (83 µmol, 62%) of the title compound as a colorless oil.

IR (film): 3700–3120, 2930, 2850, 1735, 1490, 1450, 1215, 1170, 1010, 975, 760 and 700 cm$^{-1}$

EXAMPLE 100

(8R,9S,11S,12R,15S)-9-(4-Phenylbenzyloxy)-11-hydroxy-15-(tert-butyldiphenylsilyloxy)-15-cyclohexyl-16,17,18,19,20-pentanor-5(Z),13(E)-prostadienoic Acid Methyl Ester 187.1 mg (199 µmol) of the compound prepared as per Example 101 is dissolved in 5.5 ml of anhydrous dimethylformamid, combined with 248.7 mg (2.922 mmol) of potassium nitrite, and agitated for 18 hours at 85° C. The reaction mixture is diluted with water and methylene chloride, and the organic phases are washed repeatedly with saturated sodium chloride solution. After drying with sodium sulfate, removal of the solvent, and chromatography of the residue there remains 105.6 mg (134 µmol, 69%) of the title compound as a colorless oil.

IR (film): 3700–3130, 2925, 2850, 1735, 1490, 1455, 1175, 1010, 925, 760 and 700 cm$^{-1}$

EXAMPLE 101

(8R,9S,11R,12R,15S)-9-(4-Phenylbenzyloxy)-11-(4-methylphenylsulfonyloxy)-15-(tert-butyldiphenylsilyloxy)-15-cyclohexyl-16,17,18,19,20-pentanor-5(Z),13(E)-prostadienoic Acid Methyl Ester 270.4 mg (344 mol) of the compound produced according to Example 102 is reacted in analogy to Example 14c, thus isolating after working up and purification 298 mg (318 µmol, 92%) of the title compound as a colorless oil.

IR (film): 3120–2860, 2930, 2860, 1740, 1600, 1490, 1450, 1430, 1260, 1175, 1120, 925, 820, 740 and 700 cm$^{-1}$

EXAMPLE 102

(8R,9S,11R,12R,15S)-9-(4-Phenylbenzyloxy)-11-hydroxy-15-(tert-butyldiphenylsilyloxy)-15-cyclohexyl-16,17,18,19,20-pentanor-5(Z),13(E)-prostadienoic Acid Methyl Ester 486.3 mg (559 µmol) of the compound prepared in accordance with Example 103 is reacted in analogy to Example 56, thus isolating after working up and purification 270.4 mg (344 µmol, 62%) of the title compound as a colorless oil.

IR (film): 3680–3120, 2925, 2840, 1740, 1485, 1455, 1175, 1020, 930, 760 and 700 cm$^{-1}$

EXAMPLE 103

(8R,9S,11R,12R,15S)-9-(4-Phenylbenzyloxy)-11-(tetrahydropyranyloxy)-15-(tert-butyldiphenylsilyloxy)-15-cyclohexyl-16,17,18,19,20-pentanor-5(Z),13(E)-prostadienoic Acid Methyl Ester 368.3 mg (598 mol) of the compound prepared according to Example 94 (II, polar spot) is reacted in analogy to Example 86, thus isolating after working up and purification 498.4 mg (573 µmol, 98%) of the title compound as a colorless oil.

IR (film): 2930, 2860, 1740, 1485, 1460, 1440, 1360, 1160, 1110, 830, 760 and 700 cm$^{-1}$

EXAMPLE 104

(8R,9S,11S,12R,15R)-9-(4-Phenylbenzyloxy)-11,15-dihydroxy-15-cyclohexyl-16,17,18,19,20-pentanor-5(Z),13(E)-prostadienoic Acid 19.6 mg (36 µmol) of the compound prepared as per Example 105 is saponified analogously to Example 1, thus isolating after working up 17.5 mg (33 µmol, 92%) of the title compound as a colorless oil.

IR (liqu. cap.): 3700–2200, 2920, 2850, 1710, 1485, 1450, 1240, 1065, 1010, 760 and 700 cm$^{-1}$

EXAMPLE 105

(8R,9S,11S,12R,15R)-9-(4-Phenylbenzyloxy)-11,15-dihydroxy-15-cyclohexyl-16,17,18,19,20-pentanor-5(Z),13(E)-prostadienoic Acid Methyl Ester 45.1 mg (57 mol) of the compound prepared according to Example 106 is reacted in analogy to Example 57b, thus isolating after working up and purification 19.6 mg (36 µmol, 62%) of the title compound as a colorless oil.

IR (film): 3680–3120, 2925, 2850, 1740, 1490, 1450, 1220, 1180, 975, 760 and 700 cm$^{-1}$

EXAMPLE 106

(8R,9S,11S,12R,15R)-9-(4-Phenylbenzyloxy)-11-hydroxy-15-(tert-butyldiphenylsilyloxy)-15-cyclohexyl-16,17,18,19,20-pentanor-5(Z),13(E)-prostadienoic Acid Methyl Ester 167.6 mg (178 mol) of the compound prepared according to Example 107 is reacted analogously to Example 100, thus isolating after working up and purification 45.1 mg (57 µmol, 32%) of the title compound as a colorless oil.

IR (film): 3700–3120, 2930, 2850, 1740, 1490, 1455, 1175, 1020, 930, 760 and 700 cm$^{-1}$

EXAMPLE 107

(8R,9S,11R,12R,15R)-9-(4-Phenylbenzyloxy)-11-(4-methylphenylsulfonyloxy)-15-(tert-butyldiphenylsilyloxy)-15 cyclohexyl-16,17,18,19,20-pentanor-5(Z),13(E)-prostadienoic Acid Methyl Ester 264.2 mg (336 mol) of the compound produced according to Example 108 is reacted in analogy to Example 14c, thus isolating after working up and purification 261.9 mg (278 µmol, 83%) of the title compound as a colorless oil.

IR (film): 3100–2760, 2930, 2860, 1740, 1715, 1600, 1490, 1450, 1430, 1360, 1220, 1175, 1100, 820, 760 and 700 $cm^{-1}$

EXAMPLE 108

(8R,9S,11R,12R,15R)-9-(4-Phenylbenzyloxy)-11-hydroxy-15-(tert-butyldiphenylsilyloxy)-15-cyclohexyl-16,17,18,19,20-pentanor-5(Z),13(E)-prostadienoic Acid Methyl Ester 507.7 mg (584 µmol) of the compound prepared according to Example 109 is reacted in analogy to Example 56, thus isolating after working up and purification 264.2 mg (336 µmol, 58%) of the title compound as a colorless oil.

IR (film): 3680–3120, 2930, 2840, 1735, 1485, 1460, 1220, 1175, 1100, 760 and 700 $cm^{-1}$

EXAMPLE 109

(8R,9S,11R,12R,15R)-9-(4-Phenylbenzyloxy)-11-(tetrahydropyranyloxy)-15-(tert-butyldiphenylsilyloxy)-15-cyclohexyl-16,17,18,19,20-pentanor-5(Z),13(E)-prostadienoic Acid Methyl Ester 392.1 mg (621 µmol) of the compound prepared according to Example 94 (I, nonpolar spot) is reacted in analogy to Example 86, thus isolating after working up and purification 520.9 mg (599 µmol, 96%) of the title compound as a colorless oil.

IR (film): 2930, 2860, 1735, 1485, 1455, 1440, 1355, 1110, 830, 760 and 700 $cm^{-1}$

EXAMPLE 110

(8R,9S,12R,15S)-9-(4-Phenylbenzyloxy)-15-hydroxy-15-cyclohexyl-16,17,18,19,20-pentanor-5-(Z),13(E)-prostadienoic Acid 86.9 mg (113 µmol) of the compound produced as per Example 111 is reacted analogously to Example 82, thus isolating after working up and purification 19.5 mg (38 µmol, 33%) of the title compound as a colorless oil.

IR (liqu. cap.): 3700–2300, 3010, 2920, 2850, 1705, 1490, 1450, 1410, 1390, 1345, 1310, 1175, 1020, 1010, 760 and 695 $cm^{-1}$

EXAMPLE 111

(8R,9S,12R,15 S )-9 -(4-Phenylbenzyloxy )-15-(tert-butyldiphenylsilyloxy)-15-cyclohexyl-16,17,18,19,20-pentanor-5(Z),13(E)-prostadienoic Acid Methyl Ester 110.9 mg (118 µmol) of the compound produced in accordance with Example 101 is reacted in analogy to Example 83, thus isolating after working up and purification 86.9 mg (113 µmol, 96%) of the title compound as a colorless oil.

IR (film): 2930, 2860, 1740, 1490, 1450, 1430, 1240, 1110, 825, 760 and 700 $cm^{-1}$

EXAMPLE 112

(8 R,9 S,12 R,15 R)-9 -(4- Phenylbenzyloxy)-15 -hydroxy-15-cyclohexyl-16,17,18,19,20-pentanor-5(Z),13-prostadienoic Acid 76.4 mg (99 µmol) of the compound prepared according to Example 113 is reacted in analogy to Example 82, thus isolating after working up and purification 23.2 mg (45 µmol, 45%) of the title compound as a colorless oil.

IR (liqu. cap.): 3700–2400, 2920, 2850, 1710, 1490, 1450, 1345, 1235, 1120, 1080, 1010, 970, 760 and 700 $cm^{-1}$

EXAMPLE 113

(8R,9S,12R,15R)-9-(4-Phenylbenzyloxy)-15-(tert-butyldiphenylsilyloxy)-15-cyclohexyl-16,17,18,19,20-pentanor-5(Z),13(E)-prostadienoic Acid Methyl Ester 94.3 mg (100 µmol) of the compound prepared as per Example 107 is reacted analogously to Example 83, thus isolating after working up and purification 76.4 mg (99 µmol, 99%) of the title compound as a colorless oil.

IR (film): 2930, 2860, 1740, 1490, 1450, 1430, 1365, 1115, 1070, 765 and 700 $cm^{-1}$

EXAMPLE 114

(8R,9S,11R,12R,15S,16S)-9-(4-Phenylbenzyloxy)-11,15-dihydroxy-16,21-dimethyl-5(Z),13(E)-prostadien-18ynoic Acid 56.4 mg (101 µmol) of the compound prepared as per Example 115 is saponified in analogy to Example 1, thus isolating after working up 34.9 mg (64 µmol, 62%) of the title compound as a colorless oil.

IR (liqu. cap.): 3700–2400, 2970, 2930, 1705, 1485, 1455, 1410, 1340, 1240, 1125, 1075, 1010, 970, 825, 760 and 700 $cm^{-1}$

EXAMPLE 115

(8R,9S,11R,12R,15S,16S)-9-(4-Phenylbenzyloxy)-11,15-dihydroxy-16,21-dimethyl-5(Z),13(E)-prostadien-18-ynoic Acid Methyl Ester 104.7 mg (163 mol) of the compound produced according to Example 116 (II, polar spot) is reacted in analogy to Example 56, thus isolating after working up and purification 65 mg (116 µmol, 71%) of the title compound as a colorless oil.

IR (film): 3700–3120, 2980, 2940, 1740, 1490, 1455, 1440, 1220, 1175, 1130, 1080, 1015, 975, 770 and 700 $cm^{-1}$

EXAMPLE 116

(8R,9S,11R,12R,15R,16S)-9-(4-Phenylbenzyloxy)-(11-tetrahydropyranyloxy)-15-hydroxy-16,21-dimethyl-5(Z),13(E)-prostadien-18-ynoic Acid Methyl Ester (I) and (8R,9S,11R,12R,15S,16S)-9-(4-Phenylbenzyloxy)-(11-tetrahydropyranyloxy)-15-hydroxy-16,21-dimethyl-5(Z),13(E)-prostadien-18-ynoic Acid Methyl Ester (II)

1.85 g (2,887 mmol) of the compound prepared according to Example 117 is reacted analogously to Example 78, thus isolating 852.9 mg (1.32 mmol, 46%) of title compound I (nonpolar spot) and 663 mg (1.03 mmol, 36%) of title compound II (polar spot).

IR (film), I: 3680–3200, 2940, 2880, 1740, 1490, 1455, 1440, 1360, 1240, 1140, 1080, 1025, 765 and 700 $cm^{-1}$ IR (film), II: 3680–3200, 2880, 1740, 1490, 1455, 1440, 1215, 1130, 760 and 700 $cm^{-1}$

EXAMPLE 117

(8R,9S,11R,12R,16S)-9-(4-Phenylbenzyloxy)-(11-tetrahydropyranyloxy)-15-oxo-16,21-dimethyl-5(Z),13(E)-prostadien-18-ynoic Acid Methyl Ester 2 g (3.841 mmol) of the compound prepared in accordance with Example 57a is reacted in analogy to Example 79 with the use of the corresponding phosphonate, thus isolating after working up and purification 1.857 g (2.887 mmol, 75%) of the title compound as a colorless oil.

IR (film): 2940, 2880, 1740, 1695, 1670, 1630, 1490, 1455, 1440, 1375, 1360, 1245, 1135, 1075, 1035, 765 and 700 cm$^{-1}$

EXAMPLE 118

(8R,9S,11R,12R,15R,16S)-9-(4-Phenylbenzyloxy)-11,15-dihydroxy-16,21-dimethyl-5(Z),13(E)-prostadien-18-ynoic Acid 76.64 mg (137 μmol) of the compound prepared according to Example 119 is saponified in analogy to Example 1, thus isolating after working up 67.3 mg (122 μmol, 89%) of the title compound as a colorless oil.

IR (liqu. cap.): 3700–2400, 3380, 2970, 2920, 1705, 1490, 1450, 1410, 1370, 1345, 1240, 1050, 1015, 965, 760 and 700 cm$^{-1}$

EXAMPLE 119

(8R,9S,11R,12R,15R,16S)-9-(4-Phenylbenzyloxy)-11,15-dihydroxy-16,21-dimethyl-5(Z),13(E)-prostadien-18-ynoic Acid Methyl Ester 114.5 g (178 μmol) of the compound prepared as per Example 116 (I, nonpolar spot) is reacted in analogy to Example 56, thus isolating after working up and purification 86.4 mg (86.4 μmol, 87%) of the title compound as a colorless oil.

IR (film): 3700–3120, 2970, 2940, 1740, 1490, 1455, 1440, 1350, 1250, 1215, 1075, 975, 835, 765 and 700 cm$^{-1}$

EXAMPLE 120

(8R,9S,11S,12R,15S,16S)-9-(4-Phenylbenzyloxy)-11,15-dihydroxy-16,21-dimethyl-5(Z),13(E)-prostadien-18-ynoic Acid 76.9 mg (137 μmol) of the compound prepared according to Example 121 is saponified in analogy to Example 1, thus isolating after working up 53 mg (96 μmol, 69%) of the title compound as a colorless oil.

IR (liqu. cap.): 3600–2800, 2970, 2940, 1710, 1485, 1410, 1340, 1125, 1060, 760 and 700 cm$^{-1}$

EXAMPLE 121

(8R,9S,11S,12R,15S,16S)-9-(4-Phenylbenzyloxy)-11,15-dihydroxy-16,21-dimethyl-5(Z),13(E)-prostadien-18-ynoic Acid Methyl Ester 185.5 mg (232 mol) of the compound prepared according to Example 122 is reacted in analogy to Example 36d, thus isolating after working up and purification 87.1 mg (156 μmol, 67%) of the title compound as a colorless oil.

IR (film): 3660–3100, 2970, 2930, 1735, 1490, 1455, 1435, 1240, 1220, 1120, 1015, 980, 760 and 700 cm$^{-1}$

EXAMPLE 122

(8R,9S,11S,12R,15S,16S)-9-(4-Phenylbenzyloxy)-11-hydroxy-15-(tert-butyldiphenylsilyloxy)-16,21-dimethyl-5(Z),13(E)-prostadien-18-ynoic Acid Methyl Ester 313.4 mg (332 mol) of the compound produced as per Example 123 is reacted analogously to Example 100, thus isolating after working up and purification 196 mg (246 μmol, 75%) of the title compound as a colorless oil.

IR (film): 3620–3200, 2960, 2930, 2860, 1740, 1490, 1430, 1245, 1120, 1060, 825, 765, 745 and 705 cm$^{-1}$

EXAMPLE 123

(8R,9S,11R,12R,15S,16S)-9-(4-Phenylbenzyloxy)-11(4-methylphenylsulfonyloxy)-15-(tert-butyldiphenylsilyloxy)-16,21-dimethyl-5(Z),13(E)-prostadien-18-ynoic Acid Methyl Ester 377.7 mg (474 mol) of the compound prepared according to Example 124is reacted analogously to Example 14c, thus isolating after working up and purification 420.5 mg (442 μmol, 93%) of the title compound as a colorless oil.

IR (film): 2960, 2930, 2860, 1735, 1600, 1490, 1430, 1360, 1220, 1175, 1110, 825, 765, 740 and 705 cm$^{-1}$

EXAMPLE 124

(8R,9S,11R,12R,15S,16S )-9-(4-Phenylbenzyloxy)-11-hydroxy-15-(tert-butyldiphenylsilyloxy)-16,21-dimethyl-5(Z),13(E)-prostadien-18-ynoic Acid Methyl Ester 725.7 mg (823 mol) of the compound prepared in accordance with Example 125 is reacted analogously to Example 56, thus isolating after working up and purification 388.2 mg (489 μmol, 59%) of the title compound as a colorless oil.

IR (film): 3630–3200, 2960, 2930, 2860, 1710, 1490, 1460, 1110, 1060, 975, 825, 760, 740 and 700 cm$^{-1}$

EXAMPLE 125

(8R,9S,11R,12R,15S,16S)-9-(4-Phenylbenzyloxy)-11-(tetrahydropyranyloxy)-15-(tert-butyldiphenysilyloxy)-16,21-dimethyl-5(Z),13(E)-prostadien-18-ynoic Acid Methyl Ester 558.3 mg (868 mol) of the compound produced according to Example 116 (II, polar spot) is reacted analogously to Example 86, thus isolating after working up and purification 740.1 mg (840 μmol, 97%) of the title compound as a colorless oil.

IR (film): 2960, 2930, 2860, 1740, 1590, 1430, 1360, 1110, 1080, 1030, 820, 760 and 700 cm$^{-1}$

EXAMPLE 126

(8R,9S,11S,12R,15R,16S)-9-(4-Phenylbenzyloxy)-11,15-dihydroxy-16,21-dimethyl-5(Z),13(E)-prostadien-18-ynoic Acid 65.1 mg (116 μmol) of the compound produced according to Example 127 is saponified in analogy to Example 1, thus isolating after working up and purification 22.2 mg (41 μmol, 35%) of the title compound as a colorless oil.

IR (liqu. cap.): 3700–2500, 2970, 2930, 1710, 1490, 1450, 1405, 1345, 1320, 1240, 1115, 1065, 1010, 970, 825, 760 and 700 cm$^{-1}$

EXAMPLE 127

(8R,9S,11S,12R,15R,16S)-9-(4-Phenylbenzyloxy)-11,15-dihydroxy-16,21-dimethyl-5(Z),13(E)-prostadien-18-ynoic Acid Methyl Ester 168.1 mg (211 mol) of the compound prepared as per Example 128 is reacted analogously to Example 36d, thus isolating after working up and purification 76.4 mg (119 μmol, 65%) of the title compound as a colorless oil.

IR (film): 3660–3120, 2970, 2930, 1735, 1490, 1455, 1435, 1320, 1215, 1120, 1070, 760 and 700 cm$^{-1}$

EXAMPLE 128

(8R,9S,11S,12R,15R,16S)-9-(4-Phenylbenzyloxy)-11-hydroxy-15-(tert-butyldiphenylsilyloxy)-16,21-dimethyl-5(Z), 13(E)-prostadien-18-ynoic Acid Methyl Ester 309.9 mg (326 mol) of the compound prepared according to Example 129 is reacted analogously to Example 100, thus isolating after working up 178 mg (223 μmol, 69%) of the title compound as a colorless oil.

IR (film): 3640–3200, 2960, 2930, 2860, 1740, 1490, 1460, 1430, 1375, 1245, 1110, 825, 765,740 and 705 cm$^{-1}$

EXAMPLE 129

(8R,9S,11R,12R,15R,16S)-9-(4-Phenylbenzyloxy)-11(4-methylphenylsulfonyloxy)-15-(tert-butyldiphenylsilyloxy)-16,21-dimethyl-5(Z),13(E)-prostadien-18-ynoic Acid Methyl Ester 363.2 mg (465 mol) of the compound prepared according to Example 130 is reacted in analogy to Example 14c, thus isolating after working up and purification 425.3 mg (447 µmol, 98%) of the title compound as a colorless oil.

IR (film): 2960, 2930, 2860, 1740, 1715, 1600, 1490, 1430, 1360, 1190, 1175, 1110, 925, 820, 760 and 700 cm$^{-1}$

EXAMPLE 130

(8R,9S,11R,12R,15R,16S)-9-(4-Phenylbenzyloxy)-11-hydroxy-15-(tert-butyldiphenylsilyloxy-16,21-dimethyl-5(Z), 13(E)-prostadien-18-ynoic Acid Methyl Ester 657.3 mg (746 µmol) of the compound prepared as per Example 131 is reacted analogously to Example 56, thus isolating after working up and purification 373.3 mg (468 µmol, 63%) of the title compound as a colorless oil.

IR (film): 3630–3220, 2960, 2930, 1740, 1485, 1430, 1110, 1070, 975, 760 and 700 cm$^{-1}$

EXAMPLE 131

(8R,9S,11R,12R,15R,16S)-9-(4-Phenylbenzyloxy)-11-(tetrahydropyranyloxy)-15-(tert-butyldiphenylsilyloxy)-16,21-dimethyl-5(Z),13(E)-prostadien-18-ynoic Acid Methyl Ester 500 mg (778 mol) of the compound prepared according to Example 116 (I, nonpolar spot) is reacted analogously to Example 86, thus isolating after working up and purification 670.9 mg (762 µmol, 98%) of the title compound as a colorless oil.

IR (film): 2960, 2930, 2870, 2860, 1740, 1585, 1470, 1430, 1350, 1110, 1075, 1025, 755 and 700 cm$^{-1}$

EXAMPLE 132

(8R,9S,12R,15S,16S)-9-(4-Phenylbenzyloxy)-15-hydroxy-16,21-dimethyl-5(Z),13(E)-prostadien-18-ynoic Acid 30.1 mg (55 µmol) of the compound produced as per Example 133 is saponified analogously to Example 1, thus isolating after working up and purification 17.6 mg (33 µmol, 60%) of the title compound as a colorless oil.

IR (liqu. cap.): 3600–2700, 2960, 2930, 2870, 1710, 1490, 1455, 1410, 1345, 1240, 1125, 1075, 1010, 975, 760 and 700 cm$^{-1}$

EXAMPLE 133

(8R,9S,12R,15S,16S)-9-(4-Phenylbenzyloxy)-15-hydroxy-16,21-dimethyl-5(Z),13(E)-prostadien-18-ynoic Acid Methyl Ester 75.8 mg (97 mol) of the compound prepared as in Example 134 is reacted analogously to Example 36d, thus isolating after working up and purification 30.1 mg (55 µmol, 57%) of the title compound as a colorless oil.

IR (film): 3680–3160, 2960, 2930, 1735, 1490, 1460, 1430, 1365, 1120, 825, 755 and 700 cm$^{-1}$

EXAMPLE 134

(8R,9S,12R,15S,16S)-9-(4-Phenylbenzyloxy)-15-(tert-butyldiphenylsilyloxy)-16,21-dimethyl-5(Z),13(E)-prostadien-18-ynoic Acid Methyl Ester 107.1 mg (112 mol) of the compound produced according to Example 123 is reacted analogously to Example 83, thus isolating after working up and purification 75.8 mg (97 µmol, 86%) of the title compound as a colorless oil.

IR (film): 2960, 2930, 2860, 1735, 1480, 1455, 1440, 1360, 1110, 1055, 970, 760, 740 and 700 cm$^{-1}$

EXAMPLE 135

(8R,9S,12R,15R,16S)-9-(4-Phenylbenzyloxy)-15-hydroxy-16,21-dimethyl-5(Z),13(E)-prostadien-18-ynoic acid 37.3 mg (68 µmol) of the compound produced as per Example 136 is saponified analogously to Example 1, thus isolating after working up and purification 25.8 mg (47 µmol, 71%) of the title compound as a colorless oil.

IR (liqu. cap.): 3700–2400, 2960, 2930, 2870, 1710, 1490, 1455, 1410, 1340, 1240, 1075, 1010, 970, 760 and 700 cm$^{-1}$

EXAMPLE 136

(8R,9S,12R,15R,16S)-9-(4-Phenylbenzyloxy)-15-hydroxy-16,21-dimethyl-5(Z),13(E)-prostadien-18-ynoic Acid Methyl Ester 90.1 mg (115 mol) of the compound produced according to Example 137 is reacted in analogy to Example 36d, thus isolating after working up and purification 37.3 mg (68 µmol, 60%) of the title compound as a colorless oil.

IR (film): 3700–3100, 2960, 2930, 2860, 1740, 1490, 1460, 1430, 1365, 1115, 1075, 975, 825, 765 and 700 cm$^{-1}$

EXAMPLE 137

(8R,9S,12R,15R,16S )-9-(4-Phenylbenzyloxy)-15-(tertbutyldiphenylsilyloxy)-16,21-dimethyl-5(Z),13(E)-prostadien-18-ynoic Acid Methyl Ester 115.4 mg (121 mol) of the compound produced in accordance with Example 129 is reacted in analogy to Example 83, thus isolating after working up and purification 90.1 mg (115 µmol, 95%) of the title compound as a colorless oil.

IR (film): 2955, 2930, 2855, 1735, 1485, 1455, 1440, 1360, 1110, 1060, 970, 825, 760, 740 and 700 cm$^{-1}$

EXAMPLE 138

7-[(1R,2S,4R,5S)-2-(4-Phenylbenzyloxy)-4-hydroxy-5-(4-fluorobenzyloxymethyl)cyclopentyl]-5(Z)-heptenoic Acid 62.7 mg (114 µmol) of the compound prepared as per Example 139 is saponified analogously to Example 1, thus isolating after working up and purification 35.9 mg (68 µmol, 59%) of the title compound as a colorless oil.

IR (liqu. cap.): 3680–2200, 3030, 3000, 2920, 2860, 1710, 1600, 1510, 1490, 1410, 1350, 1220, 1100, 820, 760 and 700 cm$^{-1}$

EXAMPLE 139

7-[(1R,2S,4R,5S)-2-(4-Phenylbenzyloxy)-4-hydroxy-5-(4-fluorobenzyloxymethyl)cyclopentyl]-5(Z)-heptenoic Acid Methyl Ester 403.9 mg (640 mol) of the compound prepared according to Example 140 is reacted in analogy to Example 56, thus isolating after working up and purification 309.7 mg (567 µmol, 88%) of the title compound as a colorless oil.

IR (film): 3680–3200, 2980, 2890, 1735, 1590, 1490, 1210, 1125, 1110, 1020, 765 and 700 cm$^{-1}$

EXAMPLE 140

7-[(1R,2S,4R,5S)-2-(4-Phenylbenzyloxy)-4-(tetrahydropyranyloxy)-5-(4- fluorobenzyloxymethyl)cyclopentyl]-5(Z)-heptenoic Acid Methyl Ester 500 mg (956 µmol) of the compound prepared according to Example 57b is dissolved in 0.58 ml of 4-fluorobenzyl bromide, combined with 0.95 ml of 50% strength potassium hydroxide solution and 44 mg of tetrabutylammonium hydrogen sulfate, and vigorously stirred for 21 hours at room temperature. After acidifying with 10% strength citric acid, the mixture is diluted with ether, washed with saturated sodium chloride solution, and dried over sodium sulfate. The residue obtained after filtration and solvent removal is purified by chromatography on silica gel, thus obtaining 411.9 mg (653 µmol, 68%) of the title compound as a colorless oil.

IR (film): 2950, 2870, 1735, 1600, 1510, 1490, 1455, 1440, 1360, 1205, 1020, 975, 820, 760 and 700 cm$^{-1}$

EXAMPLE 141

7-[(1R,2S,4S,5S)-2-(4-Phenylbenzyloxy)-4-hydroxy-5-(4-fluorobenzyloxymethyl)cyclopentyl]-5(Z)-heptenoic Acid 55.7 mg (102 µmol) of the compound prepared according to Example 142 is saponified in analogy to Example 1, thus isolating after working up and purification 34.7 mg (65 µmol, 64%) of the title compound as a colorless oil.

IR (liqu. cap.): 3680–2200, 3030, 2930, 2870, 1735, 1600, 1510, 1220, 1100, 850, 760 and 700 cm$^{-1}$

EXAMPLE 142

7-[(1R,2S,4S,5S)-2-(4-Phenylbenzyloxy)-4-hydroxy-5-(4-fluorobenzyloxymethyl)cyclopentyl]-5(Z)-heptenoic Acid Methyl Ester 160.4 mg (229 mol) of the compound prepared according to Example 143 is reacted analogously to Example 100, thus isolating after working up and purification 55.7 mg (102 µmol, 45%) of the title compound as a colorless oil.

IR (film): 3700–3180, 2960, 2890, 1740, 1600, 1480, 1380, 1210, 1130, 1110, 1020, 890, 760 and 700 cm$^{-1}$

EXAMPLE 143

7-[(1R,2S,4R,5S)-2-(4-Phenylbenzyloxy)-4-(4-methylphenylsulfonyloxy)-5-(4-fluorobenzyloxymethyl)cyclopentyl)cyclopentyl]-5(Z)-heptenoic Acid Methyl Ester 247 mg (452 mol) of the compound produced as per Example 139 is reacted in analogy to Example 14c, thus isolating after working up and purification 260.9 mg (372 µmol, 82%) of the title compound as a colorless oil.

IR (film): 2940, 2860, 1735, 1605, 1520, 1490, 1440, 1360, 1245, 1230, 1175, 1095, 830, 765 and 700 cm$^{-1}$

EXAMPLE 144

7-[(1R,2S,5S)-2-(4-Phenylbenzyloxy)-5-(4-fluorobenzyloxymethyl)cyclopentyl]-5(Z)-heptenoic Acid 65.7 mg (123 µmol) of the compound prepared according to Example 145 is saponified in analogy to Example 1, thus isolating after working up and purification 41 mg (80 µmol, 64%) of the title compound as a colorless oil.

IR (liqu. cap.): 3680–2400, 3040, 3010, 2940, 2860, 1710, 1600, 1510, 1410, 1220, 1080, 825, 760 and 700 cm$^{-1}$

EXAMPLE 145

7-[(1R,2S,5S)-2-(4-Phenylbenzyloxy)-5-(4-fluorobenzyloxymethyl)cyclopentyl]-5(Z)-heptenoic Acid Methyl Ester 100.5 mg (143 mol) of the compound produced according to Example 143 is reacted analogously to Example 83, thus isolating after working up and purification 65.7 mg (123 µmol, 86%) of the title compound as a colorless oil.

IR (film): 2940, 2860, 1740, 1610, 1490, 1450, 1440, 1360, 1210, 1025, 760 and 700 cm$^{-1}$

EXAMPLE 146

7-[(1R,2S,4R,5S)-2-(4-Phenylbenzyloxy)-4-hydroxy-5-(4-cyanobenzyloxymethyl)cyclopentyl]-5(Z)-heptenoic Acid 80 mg (144 µmol) of the compound prepared as per Example 147 is saponified in analogy to Example 1, thus isolating after working up and purification 41.5 mg (77 µmol, 53%) of the title compound.

IR (liqu. cap.): 3680–2400, 3030, 3000, 2910, 2860, 2230, 1710, 1610, 1490, 1410, 1250, 1100, 820, 760 and 700 cm$^{-1}$

EXAMPLE 147

7-[(1R,2S,4R,5S)-2-(4-Phenylbenzyloxy)-4-hydroxy-5-(4-cyanobenzyloxymethyl)cyclopentyl]-5(Z)-heptenoic Acid Methyl Ester 130.6 mg (206 mol) of the compound prepared as per Example 148 is reacted analogously to Example 56, thus isolating after working up and purification 80 mg (144 µmol, 70%) of the title compound.

IR (film): 3700–3200, 2950, 2880, 2215, 1740, 1610, 1490, 1455, 1370, 1210, 1025, 765 and 700 cm$^{-1}$

EXAMPLE 148

7-[(1R,2S,4R,5S)-2-(4-Phenylbenzyloxy)-4-(tetrahydropyranyloxy)-5-(4-cyanobenzyloxymethyl)cyclopentyl]-5(Z)-heptenoic Acid Methyl Ester 159.3 mg (304 µmol) of the compound prepared according to Example 57b is dissolved in 0.5 ml of toluene, combined with 299.4 mg (1.52 mmol) of 4-cyanobenzyl bromide, 0.3 ml of 50% strength potassium hydroxide solution and 13.7 mg of tetrabutylammonium hydrogen sulfate, and the mixture is vigorously stirred for 19.5 hours at room temperature. After acidifying with 10% strength citric acid, the mixture is diluted with ethyl acetate, washed with saturated sodium chloride solution, and dried over sodium sulfate. The residue obtained after filtration and solvent removal is purified by chromatography on silica gel, yielding 130.6 mg (206 µmol, 67%) of the title compound.

IR (film): 2950, 2870, 2215, 1735, 1615, 1490, 1455, 1440, 1360, 1205, 1130, 1110, 1020, 975, 820, 765 and 700 cm$^{-1}$

We claim:

1. A cyclopentane ether compound of Formula I

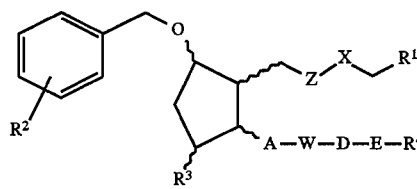

wherein

R$^1$ is

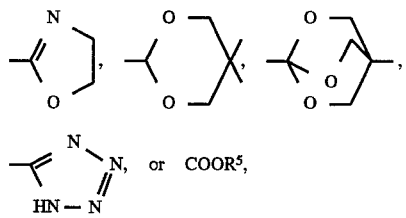

wherein

R$^5$ is hydrogen, C$_1$–C$_{10}$-alkyl optionally substituted by halogen, phenyl, C$_1$–C$_4$-alkoxy, di-(C$_1$–C$_4$)-alkylamino, C$_5$–C$_6$-cycloalkyl, C$_7$–C$_{16}$-aralkyl, γ-substituted-phenacyl, C$_6$–C$_{12}$-aryl, a 5- or 6-membered heterocyclic residue with at least one N, O or S atom, or —CONHR$^7$ wherein R$^7$ is hydrogen, C$_1$–C$_{10}$-alkanoyl, or C$_1$–C$_{10}$-alkanesulfonyl;

Z is a direct bond, (Z)—CH═CH—, (E)—CH═CH—, or —C≡C—;

X is —(CH$_2$)$_p$—, —CH$_2$—O—, or —CH$_2$—S—;

p is 0 to 5;

$R^2$ is Y or

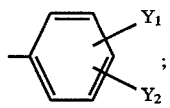

$R^3$ is hydrogen, F, $R^6$ or $OR^6$;

A is a direct bond, (Z)—CH═CH—, (E)—CH═CH—, or —C≡C—;

W is a direct bond, a —[(CH$_2$)$_n$—V]$_q$ group, a —(CH$_2$)$_n$—V—(CH$_2$)$_q$—V group, a free or functionally modified hydroxymethylene group, or a free or functionally

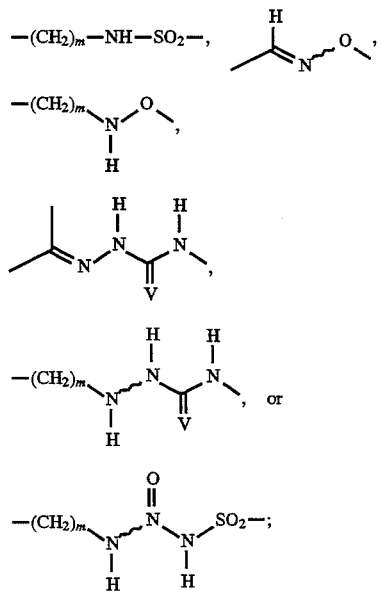

modified group wherein the hydroxy group can in each case be in the α- or β position;

q is 1 or 2;

n is 0 to 2;

D is a direct bond, a straight-chain saturated alkylene group of 1–5 carbon atoms, a branched saturated alkylene group, a straight-chain or branched unsaturated alkylene group of 2–5 carbon atoms which can optionally be substituted by fluorine atoms, m is 0 to 2;

V is an O or S atom;

E is a direct bond, —C≡C— or —CH═CR$^8$ wherein $R^8$ is hydrogen, C$_1$–C$_5$-alkyl, halogen, or trifluoromethyl;

AW, DE, independently of each other, mean a direct bond, $R^4$ is Y-substituted C$_1$–C$_{10}$-alkyl, C$_3$–C$_{10}$-cycloalkyl,

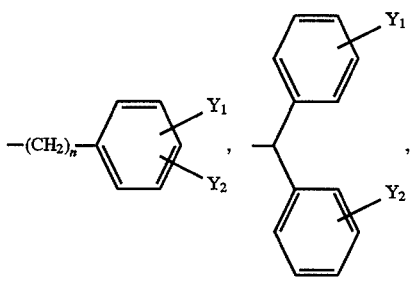

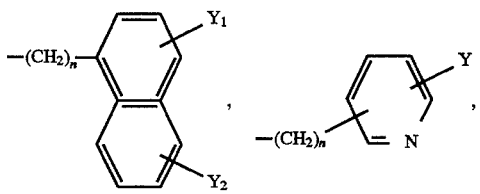

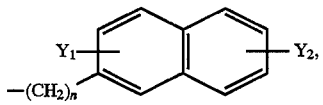

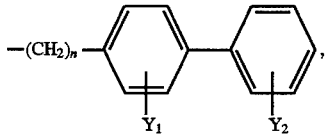

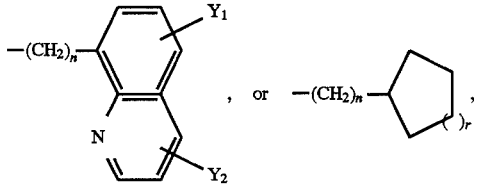

r is 1 or 2;

Y$_1$ and Y$_2$, being identical or different, are Y, wherein Y is hydrogen, halogen, CN, N$_3$, CF$_3$, OR$^6$, NO$_2$, —CH$_2$—OR$^6$, COOR$_6$ or C$_1$–C$_{10}$-alkyl;

$R^6$ is hydrogen, C$_1$–C$_{10}$-alkyl, halogen-substituted C$_6$–C$_{12}$-aryl or C$_7$–C$_{16}$-aralkyl and, if $R^5$ is hydrogen, the salts thereof with physiologically compatible bases, the α-, β- or γ-cyclodextrin clathrates, or liposome-encapsulated compounds of Formula I, with the proviso that the compound is not (9α, 11α, 15S)-9-Benzyloxy-11,15-dihydroxy-5(Z), 13(E)-prostadienic acid, its 15-epi-compound, or 9α-Benzyloxy-15-(t-butyldimethylsilyloxy)-11α-hydroxy-13(E)-prostenic acid.

2. A compound according to claim 1, wherein $R^4$, $R^5$ $R^6$, or Y is a C$_1$–C$_4$-alkyl.

3. A compound according to claim 1, wherein $R^4$ or $R^5$ is a C$_3$–C$_{10}$-cycloalkyl.

4. A compound according to claim 1, wherein $R^1$ is COOR$^5$.

5. A compound according to claim 1, wherein $R^3$ is hydrogen or hydroxy.

6. A compound according to claim 1, wherein $R^5$ is hydrogen or methyl.

7. A compound according to claim 1, wherein $R^7$ is methanesulfonyl.

8. A compound according to claim 1, wherein n is 0 or 1.

9. A compound according to claim 1, wherein p is 0–4.

10. A pharmaceutical composition comprising a compound of claim 1 and a pharmaceutically acceptable excipient.

11. 7-[1R,2S,5S)-2-(4-Phenylbenzyloxy)-5-(4-fluorophenylsulfonylamino)cyclopentyl]-5(Z)-heptenoic acid.

12. A process for the production of cyclopentane ether derivatives of Formula I, wherein the hydroxy compound of Formula II

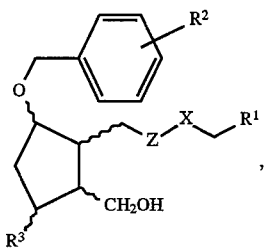
(II)

wherein

R¹ is

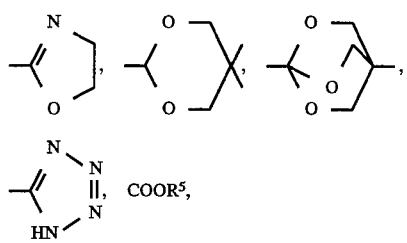

R² is Y or,

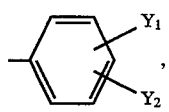

R³ is hydrogen, F, R⁶ or OR⁶,

X is —(CH)₂—O, or —CH₂—S—,

Z is a direct bond, (Z)—CH=CH—, (E)—CH=CH—, or —C≡C—,

R⁵ is hydrogen or C₁-C₁₀-alkyl optionally substituted by halogen, phenyl, C₁-C₄-alkoxy or di-(C₁-C₄)-alkylamino, C₅-C₆-cycloalkyl, C₇-C₁₆-aralkyl, Y-substituted phenacyl or —C₆-C₁₂-aryl, or a 5- or 6-membered heterocyclic residue with at least one N, O or S atom, or —CONHR⁷ wherein R⁷ means hydrogen, C₁-C₁₀-alkanoyl or C₁-C₁₀-alkanesulfonyl, R¹ is a —COOR⁵ ester group wherein R⁵ has the meanings indicated above with the exception of hydrogen, is reacted with a halogen compound of the formula Hal—WR—R⁴ (III) wherein Hal, W, and R⁴ have the above-indicated meanings, or, the hydroxy compound of Formula II after oxidation with oxalyl chloride/DMSO, is reacted with a dimethylphosphonate of Formula V

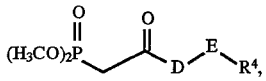
(V)

in the presence of sodium hydride or sodium hydride/bromine, and is subsequently reduced and optionally hydrogen bromide is split off or the oxidation product from II and oxalyl chloride/DMSO is reacted with an amine of the formula H₂N—O—R⁴(X) or

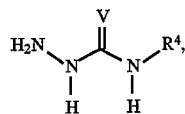
(XI)

wherein

W is a direct bond, a —[(CH₂)ₙ—V]_q group, or a —(CH₂)ₙ—V—(CH₂)_q group, a free or

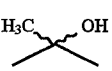

functionally modified hydroxymethylene group, a free of functionally modified group wherein the hydroxy group can in each case be in the α- or β-position.

R⁴ is a Y-substituted C₁-C₁₀-alkyl, C₃-C₁₀-cycloalkyl,

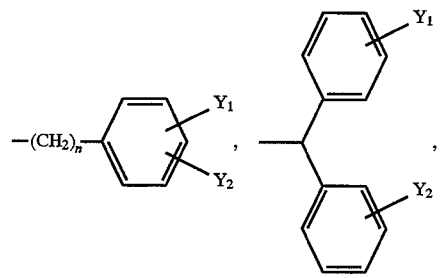

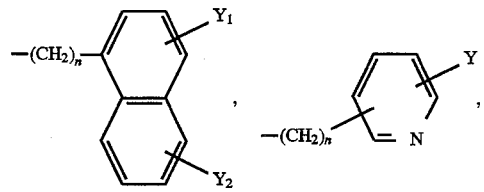

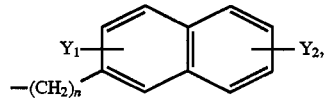

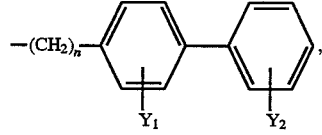

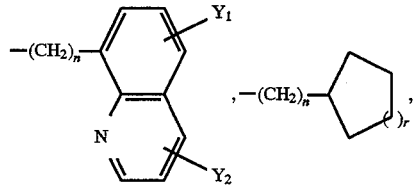

D is a direct bond, a straight-chain saturated alkylene group of 1–5 dafoon atoms, a branched saturated alkylene group, or a straight-chain or branched unsaturated alkylene group of 2–5 carbon atoms which can optionally be substituted by fluorine atoms,

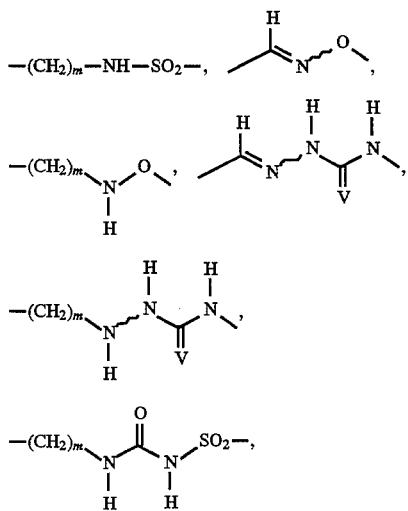

E is a direct bond, —C≡C— or —CH=CR$^8$ wherein R$^8$ means hydrogen, $C_1$–$C_5$-alkyl, halogen, or trifluoromethyl, or, the hydroxy compound of Formula II after oxidation and reaction with phosphoric acid diphenyl ester azide, 2-(trimethylsilyl)ethanol and tetrabutylammonium fluoride, the acid diphenyl ester azide, 2-(trimethylsilyl)ethanol and tetrabutylammonium fluoride, the intermediate amine of Formula VIII

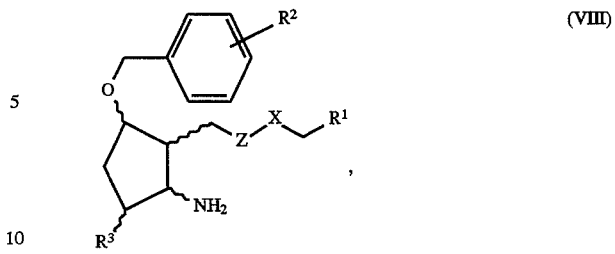

is reacted with a compound of the formula Hal—SO$_2$—R$^4$ (IX) wherein Hal and R$^4$ have the meanings set out above, or, after tosylate formulation, substitution by azide, and reduction, the intermediate amine of Formula XII

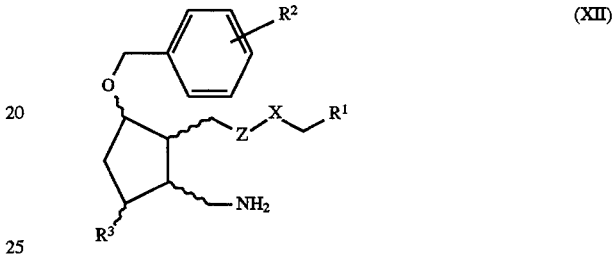

is reacted with a compound of the formula Hal—SO$_2$—R$^4$ (IX) wherein Hal and R$^4$ have the aforementioned meanings, and the resultant esters are saponified, converted into salts, converted into cyclodextrin clathrates, or encapsulated with liposomes.

* * * * *